United States Patent
Kauvar et al.

(10) Patent No.: US 9,688,744 B2
(45) Date of Patent: *Jun. 27, 2017

(54) HIGH AFFINITY HUMAN ANTIBODIES TO HUMAN CYTOMEGALOVIRUS (CMV) GB PROTEIN

(71) Applicant: Trellis Bioscience, LLC, Menlo Park, CA (US)

(72) Inventors: Lawrence M. Kauvar, San Francisco, CA (US); Stote Ellsworth, Palo Alto, CA (US); William Usinger, Lafayette, CA (US); Krista Maureen McCutcheon, Burlingame, CA (US); Ying-Ping Jiang, Lafayette, CA (US); Fen Zhang, San Francisco, CA (US); Bo Chen, Daly City, CA (US); Gizette Sperinde, El Granada, CA (US); Minha Park, Brisbane, CA (US); Orit Foord, Foster City, CA (US)

(73) Assignee: Trellis Bioscience, LLC, Menlo Park, CA (US)

(*) Notice: Subject to any disclaimer, the term of this patent is extended or adjusted under 35 U.S.C. 154(b) by 21 days.

This patent is subject to a terminal disclaimer.

(21) Appl. No.: 14/697,459

(22) Filed: Apr. 27, 2015

(65) Prior Publication Data
US 2015/0252099 A1    Sep. 10, 2015

Related U.S. Application Data

(62) Division of application No. 13/162,497, filed on Jun. 16, 2011, now Pat. No. 9,017,668.
(Continued)

(51) Int. Cl.
A61K 39/395    (2006.01)
C07K 16/08    (2006.01)
(Continued)

(52) U.S. Cl.
CPC .......... *C07K 16/088* (2013.01); *A61K 39/245* (2013.01); *C07K 16/468* (2013.01);
(Continued)

(58) Field of Classification Search
None
See application file for complete search history.

(56) References Cited

U.S. PATENT DOCUMENTS 6,642,062 B2    11/2003    Kauvar et al.
7,413,868 B2    8/2008    Kauvar et al.
(Continued)

FOREIGN PATENT DOCUMENTS

CN    101054415    10/2007
JP    2009-531273    9/2009
(Continued)

OTHER PUBLICATIONS

ACS92156.1; submitted to GenBank in 2009 by AJ Davison.
(Continued)

*Primary Examiner* — Janet L Andres
*Assistant Examiner* — Stuart W Snyder
(74) *Attorney, Agent, or Firm* — Morrison & Forester LLP

(57) ABSTRACT

Recombinant monoclonal antibodies to human cytomegalovirus (CMV) gB protein are described. The affinities of these antibodies are higher than the best previously reported antibodies. Since high affinity is critical to prevention of virus transfer across the placenta, the invention antibodies are useful as therapeutic and prophylactic agents to prevent or ameliorate effects on the fetus of CMV infection during pregnancy.

17 Claims, 2 Drawing Sheets

Related U.S. Application Data

(60) Provisional application No. 61/355,499, filed on Jun. 16, 2010.

(51) Int. Cl.
  *C07K 16/46* (2006.01)
  *A61K 39/245* (2006.01)
  *A61K 39/00* (2006.01)

(52) U.S. Cl.
  CPC ........ *A61K 2039/505* (2013.01); *C07K 16/08* (2013.01); *C07K 2317/14* (2013.01); *C07K 2317/21* (2013.01); *C07K 2317/30* (2013.01); *C07K 2317/34* (2013.01); *C07K 2317/565* (2013.01); *C07K 2317/76* (2013.01); *C07K 2317/92* (2013.01)

(56) References Cited

U.S. PATENT DOCUMENTS

| | | |
|---|---|---|
| 8,124,093 B2 | 2/2012 | Lanzavecchia et al. |
| 2005/0221400 A1 | 10/2005 | Gudas et al. |
| 2006/0177896 A1 | 8/2006 | Mach et al. |
| 2007/0280945 A1 | 12/2007 | Stevens et al. |
| 2008/0213265 A1 | 9/2008 | Lanzavecchia et al. |
| 2009/0004198 A1 | 1/2009 | Nakajima et al. |
| 2009/0042291 A1 | 2/2009 | Chu et al. |
| 2009/0324613 A1 | 12/2009 | Olsen |
| 2010/0092481 A1 | 4/2010 | Lanzavecchia et al. |

FOREIGN PATENT DOCUMENTS

| | | |
|---|---|---|
| WO | WO-03/080672 | 10/2003 |
| WO | WO-2005/045396 | 5/2005 |
| WO | WO-2007/102383 | 9/2007 |
| WO | WO-2008/008858 | 1/2008 |
| WO | WO-2009/024445 | 2/2009 |
| WO | WO-2009/111508 | 9/2009 |
| WO | WO-2009/114560 | 9/2009 |

OTHER PUBLICATIONS

ACS93398.1; submitted to GenBank in 2009 by AJ Davison.
Adler et al., Pediatr. Infect. Dis. J. (1998) 17:200-209.
Baeuerle and Reinhardt, "Bispecific T-Cell Engaging Antibodies for Cancer Therapy," Cancer Research (2009) 69:4941-4944.
CAE54372; submitted to GenBank in 2003 by McLean.
CAE54365.1; submitted to GenBank in 2003 by McLean.
Collarini et al., "Potent High-Affinity Antibodies for Treatment and Prophylaxis of Respiratory Syncytial Virus Derived from B Cells of Infected Patients," J. Immunol. (2009) 183:6338-6345.
Fitzgerald and Lugovskoy, "Rational engineering of antibody therapeutics targeting multiple oncogene pathways," MAbs (2011) 3(3):299-309.
Gicklhorn et al., "Differential effects of glycoprotein B epitope-specific antibodies on human cytomegalovirus-induced cell-cell fusion", Journal of General Virology (2003) 84(7):1859-1862.
Harriman et al., "Antibody Discovery via Multiplexed Single Cell Characterization," J. Immunol. Methods (2009) 34:135-145.
International Search Report and Written Opinion for PCT/US11/40761, mailed Feb. 3, 2012, 12 pages.
International Preliminary Report on Patentability for PCT/US11/40761, mailed May 3, 2013, 5 pages.
Lantto et al., "Binding Characteristics Determine the Neutralizing Potential of Antibody Fragments Specific for Antigenic Domain 2 on Glycoprotein B of Human Cytomegalovirus, " Virology (2003) 305:201-209.
Macagno et al., "Isolation of Human Monoclonal Antibodies That Potentially Neutralize Human Cytomegalovirus Infection by Targeting Different Epitopes on the gH/gL/UL128-131A Complex," J. Virol. (2010) 84:1005-1013.
Marshall et al., "Avidity Maturation following Immunization with Two Human Cytomegalovirus (CMV) Vaccines: A Live Attenuated Vaccine (Towne) and a Recombinant Glycoprotein Vaccine (gB/MF59)," Viral Immunol. (2003) 16:491-500.
McLean et al., "Recognition of Human Cytomegalovirus by Human Primary Immunoglobulins Identifies an Innate Foundation to an Adaptive Immune Response," J. Immunol. (2005) 174:4768-4778.
Meyer et al., "Glycoprotein gp116 of human cytomegalovirus contains epitopes for strain-common and strain specific antibodies", The Journal of General Virology (1992) 73(Pt. 9):2375-2383.
Nozawa et al., "Cytomegalovirus-specific, high-avidity IgG with neutralizing activity in maternal circulation enriched in the fetal bloodstream," J. Clin. Virol. (2009) 46(Supp 4):S58-S63.
Office Action for CN 201180038472.0, issued Oct. 27, 2014, 5 pages.
Ohlin et al., "Fine Specificity of the Human Immune Response to the Major Neutralization Epitopes Expressed on Cytomegalovirus gp58/116 (gB), as Determined with Human Monoclonal Antibodies," J. Virology (1993) 67:703-710.
Orcutt et al., "A modular IgG-scFv bispecific antibody topology," Protein Eng. Des. Sel. (2010) 23:221-228.
Park et al., "Little Role of Anti-gB Antibodies in Neutralizing Activity of Patient's Sera with Human Cytomegalovirus (HCMV) Infection," J. Korean Med. Sci. (2000) 15:133-138.
Revello et al., "In vitro selection of human cytomegalovirus variants unable to transfer virus and virus products from infected cells to polymorphonuclear leukocytes and to grow in endothelial cells," J. Gen. Virol. (2001) 82:1429-1438.
Supplementary European Search Report for EP 11796460.1, mailed Dec. 10, 2013, 9 pages.
Notice of Reason(s) for Rejection (translation) for JP 2013-515522, issued Jul. 27, 2015, 5 pages.
Office Action for CA 2,839,420, issued Feb. 20, 2017, 7 pages.
Rudikoff et al., "Single amino acid substitution altering antigen-binding specificity," Proc. Natl. Acad. Sci. USA (1982) 79:1979-1983.
Tamura et al., "Structural Correlates of an Anticarcinoma Antibody: Identification of Specificity-Determining Residues (SDRs) and Development of a Minimally Immunogenic Antibody Variant by Retention of SDRs Only," J. Immunol. (2000) 164:1432-1441.

SEQUENCE LISTING

<160> NUMBER OF SEQ ID NOS: 79

<210> SEQ ID NO 1
<211> LENGTH: 420
<212> TYPE: DNA
<213> ORGANISM: Artificial Sequence
<220> FEATURE:
<223> OTHER INFORMATION: synthetically constructed 4A2 heavy chain
      VH3-30 nucleic acid sequence
<220> FEATURE:
<221> NAME/KEY: CDS
<222> LOCATION: (1)...(420)

<400> SEQUENCE: 1

```
atg gaa ttg ggg ctg agc tgg gtt ttc gtc gtt gct ctt tta aga ggt      48
Met Glu Leu Gly Leu Ser Trp Val Phe Val Val Ala Leu Leu Arg Gly
 1               5                  10                  15 gtc cag tgt caa gtg ttg ttg gag gag tct ggg gga ggc gtg gtc cag      96
Val Gln Cys Gln Val Leu Leu Glu Glu Ser Gly Gly Gly Val Val Gln
            20                  25                  30 cct ggg agg tct ctg aga ctc tcc tgt gca ggc tct gga ttc acc ttc     144
Pro Gly Arg Ser Leu Arg Leu Ser Cys Ala Gly Ser Gly Phe Thr Phe
        35                  40                  45 aat agg cat gga att cac tgg gtc cgc cag gct cca ggc aag ggg ctg     192
Asn Arg His Gly Ile His Trp Val Arg Gln Ala Pro Gly Lys Gly Leu
    50                  55                  60 gag tgg gtg act gtt ata tca tct gat gga gca aat caa cag tat gca     240
Glu Trp Val Thr Val Ile Ser Ser Asp Gly Ala Asn Gln Gln Tyr Ala
65                  70                  75                  80 gag tcc gtg aag ggc cga ttc atc atc tcc aga gac aat tcc aag aac     288
Glu Ser Val Lys Gly Arg Phe Ile Ile Ser Arg Asp Asn Ser Lys Asn
                85                  90                  95 acg gta tat cta gaa atg aat agc ctg agg aat gac gac acg ggt gtg     336
Thr Val Tyr Leu Glu Met Asn Ser Leu Arg Asn Asp Asp Thr Gly Val
            100                 105                 110 tat ttc tgc gcg aga gac ggt cgt tgt gaa ggc gag agg tgc tac tcc     384
Tyr Phe Cys Ala Arg Asp Gly Arg Cys Glu Gly Glu Arg Cys Tyr Ser
        115                 120                 125 ggt gtc acg gac ttc tgg ggc cag gga aca ctg gtc                     420
Gly Val Thr Asp Phe Trp Gly Gln Gly Thr Leu Val
    130                 135                 140
```

<210> SEQ ID NO 2
<211> LENGTH: 140
<212> TYPE: PRT
<213> ORGANISM: Artificial Sequence
<220> FEATURE:
<223> OTHER INFORMATION: synthetically constructed 4A2 heavy chain VH3
      30 amino acid sequence
<220> FEATURE:
<221> NAME/KEY: misc_feature
<222> LOCATION: (1)...(19)
<223> OTHER INFORMATION: secretion signal sequence

<400> SEQUENCE: 2

```
Met Glu Leu Gly Leu Ser Trp Val Phe Val Val Ala Leu Leu Arg Gly
 1               5                  10                  15

Val Gln Cys Gln Val Leu Leu Glu Glu Ser Gly Gly Gly Val Val Gln
            20                  25                  30

Pro Gly Arg Ser Leu Arg Leu Ser Cys Ala Gly Ser Gly Phe Thr Phe
        35                  40                  45

Asn Arg His Gly Ile His Trp Val Arg Gln Ala Pro Gly Lys Gly Leu
    50                  55                  60
```

-continued

```
Glu Trp Val Thr Val Ile Ser Ser Asp Gly Ala Asn Gln Gln Tyr Ala
 65                  70                  75                  80

Glu Ser Val Lys Gly Arg Phe Ile Ile Ser Arg Asp Asn Ser Lys Asn
                 85                  90                  95

Thr Val Tyr Leu Glu Met Asn Ser Leu Arg Asn Asp Asp Thr Gly Val
            100                 105                 110

Tyr Phe Cys Ala Arg Asp Gly Arg Cys Glu Gly Glu Arg Cys Tyr Ser
        115                 120                 125

Gly Val Thr Asp Phe Trp Gly Gln Gly Thr Leu Val
        130                 135                 140
```

<210> SEQ ID NO 3
<211> LENGTH: 360
<212> TYPE: DNA
<213> ORGANISM: Artificial Sequence
<220> FEATURE:
<223> OTHER INFORMATION: synthetically constructed 4A2 light chain L6
      IgKV3-11 nucleic acid sequence
<220> FEATURE:
<221> NAME/KEY: CDS
<222> LOCATION: (1)...(360)

<400> SEQUENCE: 3

```
atg gaa gcc cca gcg cag ctt ctc ttc ctc ctg cta ctc tgg ctc cca      48
Met Glu Ala Pro Ala Gln Leu Leu Phe Leu Leu Leu Leu Trp Leu Pro
  1               5                  10                  15 gat acc acc gga gaa att gta ttg aca cag tct cca gcc acc ctg tct      96
Asp Thr Thr Gly Glu Ile Val Leu Thr Gln Ser Pro Ala Thr Leu Ser
             20                  25                  30 ttg tct cca ggg gag aga gcc acc ctc tcc tgc agg gcc agt cag aat     144
Leu Ser Pro Gly Glu Arg Ala Thr Leu Ser Cys Arg Ala Ser Gln Asn
         35                  40                  45 att ggc ggc tac ttg gcc tgg ttc caa caa aaa gct ggc cag gct ccc     192
Ile Gly Gly Tyr Leu Ala Trp Phe Gln Gln Lys Ala Gly Gln Ala Pro
 50                  55                  60 agg ctc ctc atc tat gat gca tcc atc agg gcc act ggc atc cca gcc     240
Arg Leu Leu Ile Tyr Asp Ala Ser Ile Arg Ala Thr Gly Ile Pro Ala
 65                  70                  75                  80 agg ttc agt ggc agt ggg tct ggg aca gac ttc act ctc acc atc agc     288
Arg Phe Ser Gly Ser Gly Ser Gly Thr Asp Phe Thr Leu Thr Ile Ser
                 85                  90                  95 agc cta gag cct gaa gat ttt gca gtt tat tac tgt cag cag cgt aac     336
Ser Leu Glu Pro Glu Asp Phe Ala Val Tyr Tyr Cys Gln Gln Arg Asn
            100                 105                 110 agt tgg cct cca ctc act ttc ggc                                     360
Ser Trp Pro Pro Leu Thr Phe Gly
        115                 120
```

<210> SEQ ID NO 4
<211> LENGTH: 120
<212> TYPE: PRT
<213> ORGANISM: Artificial Sequence
<220> FEATURE:
<223> OTHER INFORMATION: synthetically constructed 4A2 light chain L6
      IgKV3-11 amino acid sequence

<400> SEQUENCE: 4

```
Met Glu Ala Pro Ala Gln Leu Leu Phe Leu Leu Leu Leu Trp Leu Pro
  1               5                  10                  15

Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Asn
```

```
                35                  40                  45
Ile Gly Gly Tyr Leu Ala Trp Phe Gln Gln Lys Ala Gly Gln Ala Pro
         50                  55                  60

Arg Leu Leu Ile Tyr Asp Ala Ser Ile Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Asn
            100                 105                 110

Ser Trp Pro Pro Leu Thr Phe Gly
            115                 120

<210> SEQ ID NO 5
<211> LENGTH: 486
<212> TYPE: DNA
<213> ORGANISM: Artificial Sequence
<220> FEATURE:
<223> OTHER INFORMATION: synthetically constructed 19B10 heavy chain
      VH4-31 D2 J6 nucleic acid sequence
<220> FEATURE:
<221> NAME/KEY: CDS
<222> LOCATION: (1)...(486)

<400> SEQUENCE: 5 atg aaa cat ctg tgg ttc ttc ctc ctg ctg gtg gca gct ccc aga tgg      48
Met Lys His Leu Trp Phe Phe Leu Leu Leu Val Ala Ala Pro Arg Trp
  1               5                  10                  15 gtc ctg tcc cag gtg cag ctg cag cag tcg ggc cca gga ctg gtg aag      96
Val Leu Ser Gln Val Gln Leu Gln Gln Ser Gly Pro Gly Leu Val Lys
             20                  25                  30 cct tca cag acc ctg tcc ctc acc tgc act gtc tct ggt ggc tcc atc     144
Pro Ser Gln Thr Leu Ser Leu Thr Cys Thr Val Ser Gly Gly Ser Ile
         35                  40                  45 agt agc ggt gat ttt tgc tgg aat tgg atc cgc cag ccc cca ggg aag     192
Ser Ser Gly Asp Phe Cys Trp Asn Trp Ile Arg Gln Pro Pro Gly Lys
     50                  55                  60 ggc ctg gag tgg att ggg tac atc tgt tac acc ggg gac acc tac tac     240
Gly Leu Glu Trp Ile Gly Tyr Ile Cys Tyr Thr Gly Asp Thr Tyr Tyr
 65                  70                  75                  80 aac ccg ccc ctt aac agt cga gtt acc ata tca gtc gac agg tcc agg     288
Asn Pro Pro Leu Asn Ser Arg Val Thr Ile Ser Val Asp Arg Ser Arg
                 85                  90                  95 aac caa atc tcc ctg agg ctg agt tct gtg act gcc gca gac acg gcc     336
Asn Gln Ile Ser Leu Arg Leu Ser Ser Val Thr Ala Ala Asp Thr Ala
            100                 105                 110 gtg tat tat tgt gcc aga gag gat agg aga caa cta cac tct cgc ccc     384
Val Tyr Tyr Cys Ala Arg Glu Asp Arg Arg Gln Leu His Ser Arg Pro
        115                 120                 125 tac ttc tac tac ggt ttg gac gtc tgg ggc cga ggg acc aag gtc acc     432
Tyr Phe Tyr Tyr Gly Leu Asp Val Trp Gly Arg Gly Thr Lys Val Thr
    130                 135                 140 gtc tcc tca gct tcc acc aag ggc cca tcg gtc ttc ccc ctg gta ccc     480
Val Ser Ser Ala Ser Thr Lys Gly Pro Ser Val Phe Pro Leu Val Pro
145                 150                 155                 160 tct agc                                                              486
Ser Ser <210> SEQ ID NO 6
<211> LENGTH: 162
<212> TYPE: PRT
<213> ORGANISM: Artificial Sequence
```

```
<220> FEATURE:
<223> OTHER INFORMATION: synthetically constructed 19B10 heavy chain
      VH4-31 D2 J6 amino acid sequence
<220> FEATURE:
<221> NAME/KEY: misc_feature
<222> LOCATION: (1)...(19)
<223> OTHER INFORMATION: secretion signal sequence

<400> SEQUENCE: 6

Met Lys His Leu Trp Phe Phe Leu Leu Leu Val Ala Ala Pro Arg Trp
 1               5                  10                  15

Val Leu Ser Gln Val Gln Leu Gln Gln Ser Gly Pro Gly Leu Val Lys
             20                  25                  30

Pro Ser Gln Thr Leu Ser Leu Thr Cys Thr Val Ser Gly Gly Ser Ile
         35                  40                  45

Ser Ser Gly Asp Phe Cys Trp Asn Trp Ile Arg Gln Pro Pro Gly Lys
     50                  55                  60

Gly Leu Glu Trp Ile Gly Tyr Ile Cys Tyr Thr Gly Asp Thr Tyr Tyr
65                  70                  75                  80

Asn Pro Pro Leu Asn Ser Arg Val Thr Ile Ser Val Asp Arg Ser Arg
                 85                  90                  95

Asn Gln Ile Ser Leu Arg Leu Ser Ser Val Thr Ala Ala Asp Thr Ala
            100                 105                 110

Val Tyr Tyr Cys Ala Arg Glu Asp Arg Arg Gln Leu His Ser Arg Pro
        115                 120                 125

Tyr Phe Tyr Tyr Gly Leu Asp Val Trp Gly Arg Gly Thr Lys Val Thr
    130                 135                 140

Val Ser Ser Ala Ser Thr Lys Gly Pro Ser Val Phe Pro Leu Val Pro
145                 150                 155                 160

Ser Ser

<210> SEQ ID NO 7
<211> LENGTH: 420
<212> TYPE: DNA
<213> ORGANISM: Artificial Sequence
<220> FEATURE:
<223> OTHER INFORMATION: synthetically constructed 19B10 light chain A3
      IgKV2 nucleic acid sequence
<220> FEATURE:
<221> NAME/KEY: CDS
<222> LOCATION: (1)...(420)

<400> SEQUENCE: 7 atg agg ctc cct gct cag ctt ctg ggg ctg cta atg ctc tgg gtc tct        48
Met Arg Leu Pro Ala Gln Leu Leu Gly Leu Leu Met Leu Trp Val Ser
 1               5                  10                  15 gga tcc agt ggg gag att gtg atg act cag tct ccg ctc tcc ctg ccc        96
Gly Ser Ser Gly Glu Ile Val Met Thr Gln Ser Pro Leu Ser Leu Pro
             20                  25                  30 gtc acc cct gga gag acg gcc tcc atc tcc tgc agg tct agt cag agc       144
Val Thr Pro Gly Glu Thr Ala Ser Ile Ser Cys Arg Ser Ser Gln Ser
         35                  40                  45 ctc ctg cat agt aat gga cac aac tat ttg gat tgg tat ctg cag aag       192
Leu Leu His Ser Asn Gly His Asn Tyr Leu Asp Trp Tyr Leu Gln Lys
     50                  55                  60 cca ggg cag tct cca cac ctc ctg atc tat ttg ggt tct att cgg gcc       240
Pro Gly Gln Ser Pro His Leu Leu Ile Tyr Leu Gly Ser Ile Arg Ala
65                  70                  75                  80 tcc ggg gtc cct gac agg ttc agt ggc agt gga aca ggc aca gat ttt       288
Ser Gly Val Pro Asp Arg Phe Ser Gly Ser Gly Thr Gly Thr Asp Phe
                 85                  90                  95
```

```
aca ctg aaa atc agc aga gtg gag gct gag gat gtt ggg gtt tat tac     336
Thr Leu Lys Ile Ser Arg Val Glu Ala Glu Asp Val Gly Val Tyr Tyr
            100                 105                 110 tgc atg caa gct cta caa act cct aac act ttt ggc cag ggg acc aag     384
Cys Met Gln Ala Leu Gln Thr Pro Asn Thr Phe Gly Gln Gly Thr Lys
        115                 120                 125 ctg gag atc aga cga act gtg gct gca cca tct gtc                     420
Leu Glu Ile Arg Arg Thr Val Ala Ala Pro Ser Val
    130                 135                 140

<210> SEQ ID NO 8
<211> LENGTH: 140
<212> TYPE: PRT
<213> ORGANISM: Artificial Sequence
<220> FEATURE:
<223> OTHER INFORMATION: synthetically constructed 19B10 light chain A3
      IgKV2 amino acid sequence

<400> SEQUENCE: 8

Met Arg Leu Pro Ala Gln Leu Leu Gly Leu Leu Met Leu Trp Val Ser
 1               5                  10                  15

Gly Ser Ser Gly Glu Ile Val Met Thr Gln Ser Pro Leu Ser Leu Pro
            20                  25                  30

Val Thr Pro Gly Glu Thr Ala Ser Ile Ser Cys Arg Ser Ser Gln Ser
        35                  40                  45

Leu Leu His Ser Asn Gly His Asn Tyr Leu Asp Trp Tyr Leu Gln Lys
    50                  55                  60

Pro Gly Gln Ser Pro His Leu Leu Ile Tyr Leu Gly Ser Ile Arg Ala
65                  70                  75                  80

Ser Gly Val Pro Asp Arg Phe Ser Gly Ser Gly Thr Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Asn Thr Phe Gly Gln Gly Thr Lys
        115                 120                 125

Leu Glu Ile Arg Arg Thr Val Ala Ala Pro Ser Val
    130                 135                 140

<210> SEQ ID NO 9
<211> LENGTH: 330
<212> TYPE: PRT
<213> ORGANISM: Homo sapiens
<220> FEATURE:
<221> NAME/KEY: CHAIN
<222> LOCATION: (1)...(330)
<223> OTHER INFORMATION: IgG1 heavy chain amino acid sequence of
      constant region

<400> SEQUENCE: 9

Ala Ser Thr Lys Gly Pro Ser Val Phe Pro Leu Val Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 123
<212> TYPE: PRT
<213> ORGANISM: Artificial Sequence
<220> FEATURE:
<223> OTHER INFORMATION: synthetically constructed MAB297 heavy chain
      variable domain amino acid sequence

<400> SEQUENCE: 10

Gln Val Gln Leu Val Gln Ser Gly Gly Gly Val Val Gln Pro Gly Arg
1               5                   10                  15

Ser Leu Arg Leu Ser Cys Ser Ala Ser Gly Phe Thr Phe Ser Asn Tyr
            20                  25                  30

Asn Met His Trp Val Arg Gln Ala Pro Gly Lys Gly Pro Glu Trp Val
        35                  40                  45

Ala Val Ile Ser Lys Asp Gly Asn Glu Lys His Tyr Ala Glu Ser Ala
    50                  55                  60

Lys Gly Arg Phe Thr Ile Ser Arg Asp Asn Ser Lys Asn Thr Leu Tyr
65                  70                  75                  80

Met Glu Met His Ser Leu Thr Pro Glu Asp Thr Ala Met Tyr Tyr Cys
                85                  90                  95

Thr Arg Asp Gly Arg Thr Asp Gly Thr Gly Tyr Ser Gly Ile Leu Asp
            100                 105                 110

Ile Trp Gly Gln Gly Thr Lys Val Ile Val Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: synthetically constructed MAB309 and MAB318
      heavy chain variable domain amino acid sequence

<400> SEQUENCE: 11

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Met Phe Asn Thr Tyr
            20                  25                  30

Asn Met His Trp Val Arg Gln Ala Pro Gly Lys Gly Leu Glu Trp Val
        35                  40                  45

Ala Val Ile Ser Asn Asp Gly Thr Tyr Lys His Phe Ala Asp Ser Leu
    50                  55                  60

Lys Gly Arg Phe Ser Ile Ser Arg Asp Asp Ser Lys Asn Thr Leu Tyr
65                  70                  75                  80

Leu His Met Asn Ser Leu Arg Pro Asp Asp Thr Ala Ile Tyr Tyr Cys
                85                  90                  95

Ala Arg Asp Gly Arg Ser Val Gly Gly Phe Ser Gly Ile Leu Asp Pro
            100                 105                 110

Trp Gly Gln Gly Thr Leu Val Thr Val Ser Ser
        115                 120

<210> SEQ ID NO 12
<211> LENGTH: 123
<212> TYPE: PRT
<213> ORGANISM: Artificial Sequence
<220> FEATURE:
<223> OTHER INFORMATION: synthetically constructed MAB310 heavy chain
      variable domain amino acid sequence

<400> SEQUENCE: 12

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Met Phe Asn Thr Tyr
            20                  25                  30

Asn Met His Trp Val Arg Gln Ala Pro Gly Lys Gly Leu Glu Trp Val
        35                  40                  45

Ala Val Ile Ser Asn Asp Gly Thr Tyr Lys Tyr Ser Ala Asp Ser Leu
    50                  55                  60

Lys Gly Arg Phe Ser Ile Ser Arg Asp Asn Ser Lys Asn Thr Leu Tyr
65                  70                  75                  80

Leu His Met Asn Ser Leu Arg Pro Asp Asp Thr Ala Val Tyr Tyr Cys
                85                  90                  95

Ala Arg Asp Gly Arg Ser Val Gly Gly Phe Ser Gly Ile Leu Asp Pro
            100                 105                 110

Trp Gly Gln Gly Thr Leu Val Thr Val Ser Ser
        115                 120

<210> SEQ ID NO 13
<211> LENGTH: 123
<212> TYPE: PRT
<213> ORGANISM: Artificial Sequence
<220> FEATURE:
<223> OTHER INFORMATION: synthetically constructed MAB313 heavy chain
    variable domain amino acid sequence

<400> SEQUENCE: 13

Gln Val Gln Leu Val Gln Ser Gly Gly Gly Val Ile Gln Pro Gly Arg
1               5                   10                  15

Ser Leu Thr Leu Ser Cys Ala Ala Ser Gly Phe Thr Phe Ser Ala Tyr
            20                  25                  30

Ser Leu His Trp Val Arg Gln Ala Pro Gly Lys Gly Leu Gln Trp Val
        35                  40                  45

Ala Val Ile Ser Phe Asp Gly Asn Phe Lys His Phe Ala Asp Ser Leu
    50                  55                  60

Arg Gly Arg Phe Thr Ile Ser Arg Asp Asn Ser Lys Asn Arg Phe Tyr
65                  70                  75                  80

Leu Gln Met Asn Gly Leu Arg Gly Glu Asp Thr Ala Val Tyr Tyr Cys
                85                  90                  95

Ala Arg Asp Gly Arg Ala Val Asp Gly Phe Ser Gly Ile Leu Asp Phe
            100                 105                 110

Trp Gly Gln Gly Thr Leu Val Ser Val Ser Ser
        115                 120

<210> SEQ ID NO 14
<211> LENGTH: 123
<212> TYPE: PRT
<213> ORGANISM: Artificial Sequence
<220> FEATURE:
<223> OTHER INFORMATION: synthetically constructed MAB314 heavy chain
    variable domain amino acid sequence

<400> SEQUENCE: 14

Gln Val Gln Leu Gln Glu Ser Gly Gly Gly Leu Val Gln Pro Gly Gly
1               5                   10                  15

Ser Leu Lys Leu Ser Cys Ala Val Ser Gly Phe Ser Phe Gly Gly Ser
            20                  25                  30

Ala Met His Trp Val Arg Gln Ala Ser Gly Lys Gly Leu Glu Trp Ile
        35                  40                  45

Gly His Ile Arg Ser Gly Ala Asn Asn Phe Glu Thr Ala Tyr Ala Pro
    50                  55                  60

Ser Leu Asp Gly Arg Phe Thr Ile Ser Arg Asp Asp Ser Lys Asn Thr
65                  70                  75                  80

Ala Tyr Leu His Met Asn Ser Leu Lys Thr Asp Asp Thr Ala Met Tyr
                85                  90                  95

Phe Cys Thr Thr Gly Leu Ile Ala Ser Gly Asp Ala Asn Phe Asp Tyr
            100                 105                 110

Trp Gly Gln Gly Thr Gln Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: synthetically constructed MAB316 heavy chain
    variable domain amino acid sequence

<400> SEQUENCE: 15

Gln Val Gln Leu Val Gln Ser Gly Gly Gly Val Val Gln Pro Gly Arg
1               5                   10                  15

```
Ser Leu Thr Leu Ser Cys Ala Ala Ser Gly Phe Thr Phe Ser Gly Phe
            20                  25                  30

Ser Leu His Trp Val Arg Gln Ala Pro Gly Lys Gly Leu Gln Trp Val
        35                  40                  45

Ala Val Ile Ser Phe Asp Gly Asn His Lys His Phe Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Ile Asn Asp Leu Arg Gly Glu Asp Thr Ala Val Tyr Tyr Cys
                85                  90                  95

Ala Arg Asp Gly Arg Ala Val Asp Gly Phe Ser Gly Ile Leu Asp Phe
            100                 105                 110

Trp Gly Gln Gly Thr Leu Val Ser Val Ser Ser
            115                 120

<210> SEQ ID NO 16
<211> LENGTH: 123
<212> TYPE: PRT
<213> ORGANISM: Artificial Sequence
<220> FEATURE:
<223> OTHER INFORMATION: synthetically constructed MAB319 heavy chain
      variable domain amino acid sequence

<400> SEQUENCE: 16

Gln Val Gln Leu Val Glu Ser Gly Gly Val Val Gln Pro Gly Arg
1               5                   10                  15

Ser Leu Arg Leu Ser Cys Ser Ala Ser Gly Phe Thr Phe Ser Asp Tyr
            20                  25                  30

Asn Leu His Trp Val Arg Gln Ala Pro Gly Lys Gly Leu Glu Trp Val
        35                  40                  45

Ala Val Ile Ser Ile Asp Gly Ser Asp Lys His His Ala Asp Ser Val
    50                  55                  60

Lys Gly Arg Phe Thr Val Ser Arg Asp Asn Ser Lys Asn Thr Val Ser
65                  70                  75                  80

Leu Gln Met Asp Ser Leu Arg Pro Glu Asp Thr Ala Val Tyr Tyr Cys
                85                  90                  95

Ala Arg Asp Gly Arg Ser Val Gly Gly Tyr Ser Gly Ile Leu Asp Pro
            100                 105                 110

Trp Gly Gln Gly Thr Leu Val Thr Val Ser Ser
            115                 120

<210> SEQ ID NO 17
<211> LENGTH: 128
<212> TYPE: PRT
<213> ORGANISM: Artificial Sequence
<220> FEATURE:
<223> OTHER INFORMATION: synthetically constructed MAB321 heavy chain
      variable domain amino acid sequence

<400> SEQUENCE: 17

Glu Val Gln Leu Val Glu Ser Gly Ala Glu Val Lys Lys Pro Gly Glu
1               5                   10                  15

Ser Leu Lys Ile Ser Cys Gln Gly Ser Gly Tyr Arg Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr His Pro Ser Phe
    50                  55                  60
```

Gln Gly Gln Val Thr Ile Ser Ser Asp Lys Ser Leu Asn Thr Ala Tyr
65                  70                  75                  80

Leu Gln Trp Ser Ser Leu Lys Pro Ser Asp Thr Ala Val Tyr Tyr Cys
            85                  90                  95

Ala Arg His His Cys Leu Ser Thr Asn Cys Gln Thr Ala Val Ala Gly
        100                 105                 110

Tyr Asn Asp Tyr Trp Gly Gln Gly Asn Pro Gly Arg Arg Leu Leu Ser
        115                 120                 125

```
<210> SEQ ID NO 18
<211> LENGTH: 124
<212> TYPE: PRT
<213> ORGANISM: Artificial Sequence
<220> FEATURE:
<223> OTHER INFORMATION: synthetically constructed MAB322 heavy chain
      variable domain amino acid sequence

<400> SEQUENCE: 18
```

Gln Val Gln Leu Val Gln Ser Gly Gly Gly Val Val Gln Pro Gly Arg
1               5                   10                  15

Ser Leu Arg Leu Ser Cys Ser Ala Ser Gly Phe Thr Phe Thr Asn Tyr
            20                  25                  30

Asn Met His Trp Val Arg Gln Ala Pro Gly Lys Gly Leu Glu Trp Val
        35                  40                  45

Ala Val Thr Ser Lys Asp Gly Asn Glu Lys His Phe Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Thr Leu Thr Ala Glu Asp Thr Ala Ile Tyr Tyr Cys
            85                  90                  95

Thr Arg Asp Gly Arg Thr Asp Gly Thr Gly Tyr Ser Gly Ile Leu Asp
        100                 105                 110

Ile Trp Gly Gln Gly Thr Lys Val Thr Val Ser Ser
        115                 120

```
<210> SEQ ID NO 19
<211> LENGTH: 124
<212> TYPE: PRT
<213> ORGANISM: Artificial Sequence
<220> FEATURE:
<223> OTHER INFORMATION: synthetically constructed MAB323 heavy chain
      variable domain amino acid sequence

<400> SEQUENCE: 19
```

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Ala Met His Trp Val Arg Gln Ala Pro Gly Lys Gly Leu Glu Trp Val
        35                  40                  45

Ala Val Ile Ser Asn Ala Gly Arg Glu Thr His Tyr Ala Asp Ser Val
    50                  55                  60

Lys Gly Arg Phe Thr Val Ser Arg Asp Asn Ser Lys Asn Met Leu Ser
65                  70                  75                  80

Leu Gln Met Asn Ser Leu Arg Gly Glu Asp Thr Ala Val Tyr Tyr Cys
            85                  90                  95

Ala Arg Asp Gly Arg Thr Asp Gly Ser Gly Tyr Ser Gly Val Leu Asp
        100                 105                 110

-continued

Ile Trp Ala Gln Gly Thr Leu Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: synthetically constructed MAB338 heavy chain
      variable domain amino acid sequence

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ser Gly Ser Gly Phe Thr Phe Ser Asp Tyr
            20                  25                  30

Asn Leu His Trp Val Arg Gln Ala Pro Gly Lys Gly Leu Glu Trp Val
        35                  40                  45

Ala Val Ile Ser Ile Asp Gly Thr Asn Lys His His Ala Asp Ser Val
    50                  55                  60

Lys Gly Arg Phe Thr Ile Ser Arg Asp Asn Ser Lys Asn Thr Val Asn
65                  70                  75                  80

Leu Glu Met Ser Arg Leu Lys Ala Glu Asp Thr Ala Val Tyr Tyr Cys
                85                  90                  95

Val Arg Asp Gly Arg Ser Ile Gly Tyr Ser Gly Ile Phe Asp Pro
            100                 105                 110

Trp Gly Gln Gly Thr Leu Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: synthetically constructed MAB343 heavy chain
      variable domain amino acid sequence

<400> SEQUENCE: 21

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Asn Met His Trp Val Arg Gln Ala Pro Gly Lys Gly Leu Glu Trp Val
        35                  40                  45

Ala Val Ile Ser Asn Asp Gly Thr Tyr Lys Tyr Ser Ala Asp Ser Val
    50                  55                  60

Lys Gly Arg Phe Ser Ile Ser Arg Gly Asn Ser Lys Asn Thr Leu Tyr
65                  70                  75                  80

Leu Gln Met Asn Ser Leu Arg Pro Asp Asp Thr Ala Val Tyr Tyr Cys
                85                  90                  95

Ala Arg Asp Gly Arg Ser Val Gly Gly Phe Ser Gly Ile Leu Asp Pro
            100                 105                 110

Trp Gly Gln Gly Thr Leu Ala Thr Val Ser Ser
        115                 120

<210> SEQ ID NO 22
<211> LENGTH: 123
<212> TYPE: PRT
<213> ORGANISM: Artificial Sequence
<220> FEATURE:

<223> OTHER INFORMATION: synthetically constructed MAB345 heavy chain
      variable domain amino acid sequence

<400> SEQUENCE: 22

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asp Tyr
                20                  25                  30

Asn Met His Trp Val Arg Gln Ala Pro Gly Lys Gly Leu Glu Trp Val
            35                  40                  45

Ala Val Ile Ser Ile Asp Gly Thr Tyr Lys Tyr Ser Ala Asp Ser Val
        50                  55                  60

Ala Gly Arg Phe Ser Leu Ser Arg Asp Asn Ser Lys Asn Thr Leu Tyr
65                  70                  75                  80

Leu Gln Met Asn Ser Leu Arg Pro Asp Asp Thr Ala Ile Tyr Tyr Cys
                85                  90                  95

Ala Arg Asp Gly Arg Ser Val Gly Gly Phe Ser Gly Ile Leu Asp Pro
            100                 105                 110

Trp Gly Gln Gly Thr Leu Val Thr Val Ser Ser
        115                 120

<210> SEQ ID NO 23
<211> LENGTH: 106
<212> TYPE: PRT
<213> ORGANISM: Homo sapiens
<220> FEATURE:
<221> NAME/KEY: CHAIN
<222> LOCATION: (1)...(106)
<223> OTHER INFORMATION: light chain amino acid sequence of constant
      kappa region

<400> SEQUENCE: 23

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 24
<211> LENGTH: 109
<212> TYPE: PRT
<213> ORGANISM: Artificial Sequence
<220> FEATURE:
<223> OTHER INFORMATION: synthetically constructed MAB297 and MAB322
      light chain variable domain amino acid sequence

<400> SEQUENCE: 24

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Gly Gly Tyr
                20                  25                  30

```
Leu Ala Trp Tyr Gln Gln Lys Pro Asp Gln Ala Pro Arg Leu Leu Ile
            35                  40                  45

Tyr Asp Val Ser Asn Arg Ala Ala Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Thr Trp Pro Pro
                 85                  90                  95

Leu Thr Phe Gly Gly Gly Thr Lys Val Glu Ile Lys Arg
            100                 105
```

<210> SEQ ID NO 25
<211> LENGTH: 109
<212> TYPE: PRT
<213> ORGANISM: Artificial Sequence
<220> FEATURE:
<223> OTHER INFORMATION: synthetically constructed MAB309 light chain
      variable domain amino acid sequence

<400> SEQUENCE: 25

```
Glu Ile Val Leu Thr Gln Ser Pro Ala Thr Leu Ser Leu Ser Pro Gly
 1               5                  10                  15

Asp Arg Ala Thr Leu Ser Cys Arg Ala Ser Gln Thr Val Gly Arg Tyr
             20                  25                  30

Leu Ala Trp Tyr Gln Gln Lys Pro Gly Gln Ala Pro Arg Leu Leu Ile
            35                  40                  45

Tyr Asp Ala Ser Asp Arg Ala Thr Gly Ile Ser Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Ser Trp Pro Pro
                 85                  90                  95

Leu Thr Phe Gly Gly Gly Thr Lys Val Glu Ile Lys Arg
            100                 105
```

<210> SEQ ID NO 26
<211> LENGTH: 109
<212> TYPE: PRT
<213> ORGANISM: Artificial Sequence
<220> FEATURE:
<223> OTHER INFORMATION: synthetically constructed MAB310 light chain
      variable domain amino acid sequence

<400> SEQUENCE: 26

```
Glu Ile Val Leu Thr Gln Ser Pro Ala Thr Leu Ser Leu Ser Pro Gly
 1               5                  10                  15

Asp Arg Ala Thr Leu Ser Cys Arg Ala Ser Gln Thr Val Gly Arg Tyr
             20                  25                  30

Leu Ala Trp Tyr Gln Gln Lys Pro Gly Gln Ala Pro Arg Leu Leu Ile
            35                  40                  45

Tyr Asp Ala Ser Asp Arg Ala Thr Gly Ile Ser Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Leu Thr Phe Gly Gly Gly Thr Lys Val Glu Ile Lys Arg
            100                 105
```

-continued

```
<210> SEQ ID NO 27
<211> LENGTH: 108
<212> TYPE: PRT
<213> ORGANISM: Artificial Sequence
<220> FEATURE:
<223> OTHER INFORMATION: synthetically constructed MAB313 light chain
      variable domain amino acid sequence

<400> SEQUENCE: 27

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Gly Arg Tyr
            20                  25                  30

Leu Thr Trp Phe Gln Gln Lys Pro Gly Gln Ala Pro Arg Leu Leu Ile
        35                  40                  45

Tyr Asp Ala Ser Glu Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Trp Pro Pro
                85                  90                  95

Leu Thr Phe Gly Gly Gly Thr Lys Val Glu Ile Lys
            100                 105

<210> SEQ ID NO 28
<211> LENGTH: 108
<212> TYPE: PRT
<213> ORGANISM: Artificial Sequence
<220> FEATURE:
<223> OTHER INFORMATION: synthetically constructed MAB314 light chain
      variable domain amino acid sequence

<400> SEQUENCE: 28

Glu Ile Val Met Thr Gln Ser Pro Gly Thr Leu Ser Leu Phe Pro Gly
 1               5                  10                  15

Glu Arg Ala Thr Leu Ser Cys Arg Ala Ser Gln Thr Val Arg Asn Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Glu Thr Asp Phe Thr Leu Ser Ile Thr Arg Val Glu
65                  70                  75                  80

Pro Glu Asp Phe Ala Val Tyr Tyr Cys Gln Gln Tyr Gly Arg Leu Ser
                85                  90                  95

Ser Thr Phe Gly Gln Gly Thr Lys Leu Asp Leu Lys
            100                 105

<210> SEQ ID NO 29
<211> LENGTH: 108
<212> TYPE: PRT
<213> ORGANISM: Artificial Sequence
<220> FEATURE:
<223> OTHER INFORMATION: synthetically constructed MAB316 light chain
      variable domain amino acid sequence

<400> SEQUENCE: 29

Glu Ile Val Met Thr Gln Ser Pro Ala Thr Leu Ser Leu Ser Pro Gly
 1               5                  10                  15
```

Glu Arg Ala Thr Leu Ser Cys Arg Ala Ser Gln Ser Val Gly Arg Tyr
            20                  25                  30

Leu Thr Trp Phe Gln Gln Lys Pro Gly Gln Ala Pro Arg Leu Leu Ile
        35                  40                  45

Tyr Asp Ala Ser Glu Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 30
<211> LENGTH: 108
<212> TYPE: PRT
<213> ORGANISM: Artificial Sequence
<220> FEATURE:
<223> OTHER INFORMATION: synthetically constructed MAB318 light chain
      variable domain amino acid sequence

<400> SEQUENCE: 30

Glu Val Val Leu Thr Gln Ser Pro Ala Thr Leu Ser Leu Ser Pro Gly
1               5                   10                  15

Asp Arg Ala Thr Leu Ser Cys Arg Ala Ser Gln Thr Val Gly Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asp Arg Ala Thr Gly Ile Ser Ala Arg Phe Ser Gly
    50                  55                  60

Ser Gly Ser Gly Thr Asp Phe Thr Leu Thr Ile Gly Ser Leu Glu Pro
65                  70                  75                  80

Glu Asp Phe Ala Val Tyr Tyr Cys Gln Gln Arg Ser Ser Trp Pro Pro
                85                  90                  95

Leu Thr Phe Gly Gly Gly Thr Lys Val Glu Ile Lys
            100                 105

<210> SEQ ID NO 31
<211> LENGTH: 108
<212> TYPE: PRT
<213> ORGANISM: Artificial Sequence
<220> FEATURE:
<223> OTHER INFORMATION: synthetically constructed MAB319 light chain
      variable domain amino acid sequence

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Glu Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Ala Val Tyr Tyr Cys Gln Gln Arg Asn Asn Trp Pro Pro
                85                  90                  95

Leu Thr Phe Gly Gly Gly Thr Lys Val Glu Ile Lys
            100                 105

<210> SEQ ID NO 32
<211> LENGTH: 113
<212> TYPE: PRT
<213> ORGANISM: Artificial Sequence
<220> FEATURE:
<223> OTHER INFORMATION: synthetically constructed MAB321 light chain
      variable domain amino acid sequence

<400> SEQUENCE: 32

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Ile Leu Phe Ser
             20                  25                  30

Ser Lys Asn Gln Asn His Leu Ala Trp Tyr Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                 85                  90                  95

Tyr Tyr Asn Ile Pro His Thr Phe Gly Gly Gly Thr Lys Val Glu Ile
            100                 105                 110

Lys

<210> SEQ ID NO 33
<211> LENGTH: 107
<212> TYPE: PRT
<213> ORGANISM: Artificial Sequence
<220> FEATURE:
<223> OTHER INFORMATION: synthetically constructed MAB323 light chain
      variable domain amino acid sequence

<400> SEQUENCE: 33

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Arg Tyr
             20                  25                  30

Leu Ala Trp Phe Gln His Arg Pro Gly Gln Pro Pro Arg Leu Leu Ile
         35                  40                  45

Tyr Asp Ala Ser Lys Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 34
<211> LENGTH: 108
<212> TYPE: PRT
<213> ORGANISM: Artificial Sequence
<220> FEATURE:
<223> OTHER INFORMATION: synthetically constructed MAB338 light chain
      variable domain amino acid sequence

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Gln Arg Ala Thr Gly Ile Pro Ala Arg Phe Ser Gly
50                  55                  60

Ser Gly Ser Gly Thr Asp Phe Thr Leu Ala Ile Ser Ser Leu Glu Pro
65                  70                  75                  80

Glu Asp Val Ala Val Tyr Tyr Cys Gln Gln Arg Ser Asn Trp Pro Pro
                85                  90                  95

Leu Thr Phe Gly Gly Gly Thr Lys Ile Glu Ile Lys
            100                 105

<210> SEQ ID NO 35
<211> LENGTH: 108
<212> TYPE: PRT
<213> ORGANISM: Artificial Sequence
<220> FEATURE:
<223> OTHER INFORMATION: synthetically constructed MAB343 light chain
      variable domain amino acid sequence

<400> SEQUENCE: 35

Glu Ile Val Met Thr Gln Ser Pro Ala Thr Leu Ser Leu Ser Pro Gly
1               5                   10                  15

Asp Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asp Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 36
<211> LENGTH: 108
<212> TYPE: PRT
<213> ORGANISM: Artificial Sequence
<220> FEATURE:
<223> OTHER INFORMATION: synthetically constructed MAB345 light chain
      variable domain amino acid sequence

<400> SEQUENCE: 36

Glu Ile Val Met Thr Gln Ser Pro Ala Thr Leu Ser Leu Ser Pro Gly
1               5                   10                  15

Asp Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Met
        35                  40                  45

Tyr Asp Ser Ser Val Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Pro
            85                  90                  95

Leu Thr Phe Gly Gly Gly Thr Lys Val Glu Ile Lys
            100                 105

<210> SEQ ID NO 37
<211> LENGTH: 1599
<212> TYPE: DNA
<213> ORGANISM: Homo sapiens
<220> FEATURE:
<221> NAME/KEY: misc_feature
<222> LOCATION: (1)...(1599)
<223> OTHER INFORMATION: IgG1 heavy chain nucleotide sequence of
      constant region
<220> FEATURE:
<221> NAME/KEY: intron
<222> LOCATION: (289)...(685)
<220> FEATURE:
<221> NAME/KEY: intron
<222> LOCATION: (731)...(848)
<220> FEATURE:
<221> NAME/KEY: intron
<222> LOCATION: (1208)...(1277)

<400> SEQUENCE: 37
gcctccacca agggcccatc agtcttcccc ctggcaccct ctaccaagag cacctctggg     60
ggcacaacgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttggtgag    300
aggccagcac agggagggag ggtgtctgct ggaagccagg ctcagcgctc ctgcctggac    360
gcatcccggc tatgcagtcc cagtccaggg cagcaaggca ggccccgtct gcctcttcac    420
ccggaggcct ctgcccgccc cactcatgct caggagaggg tcttctggc tttttccccca    480 ggctctgggc aggcacaggc taggtgcccc taacccaggc cctgcacaca aggggcagg    540 tgctgggctc agacctgcca agagccatat ccgggaggac cctgcccctg acctaagccc    600
accccaaagg ccaaactctc cactccctca gctcggacac cttctctcct cccagattcc    660
agtaactccc aatcttctct ctgcagagcc caaatcttgt gacaaaactc acacatgccc    720
accgtgccca ggtaagccag cccaggcctc gccctccagc tcaaggcggg acaggtgccc    780
tagagtagcc tgcatccagg acaggcccc agccgggtgc tgacacgtcc acctccatct    840
cttcctcagc acctgaactc ctggggggac cgtcagtctt cctcttcccc ccaaaaccca    900
aggacaccct catgatctcc cggacccctg aggtcacatg cgtggtggtg gacgtgagcc    960
acgaagaccc tgaggtcaag ttcaactggt acgtggacgg cgtggaggtg cataatgcca   1020
agacaaagcc gcgggaggag cagtacaaca gcacgtaccg tgtggtcagc gtcctcaccg   1080
tcctgcacca ggactggctg aatggcaagg agtacaagtg caaggtctcc aacaaagccc   1140
tcccagcccc catcgagaaa accatctcca aagccaaagg tgggacccgt ggggtgcgag   1200
ggccacatgg acagaggccg gctcggccca cctctgccc tgagagtgac cgctgtacca   1260
acctctgtcc ctacagggca gccccgagaa ccacaggtgt acaccctgcc ccatcccgg   1320 gaggagatga ccaagaacca ggtcagcctg acctgcctgg tcaaaggctt ctatcccagc   1380
gacatcgccg tggagtggga gagcaatggg cagccggaga caactacaa gaccacgcct   1440 cccgtgctgg actccgacgg ctccttcttc ctctatagca agctcaccgt ggacaagagc   1500
aggtggcagc aggggaacgt cttctcatgc tccgtgatgc atgaggctct gcacaaccac   1560
tacacgcaga agagcctctc cctgtccccg ggtaaatga                         1599

<210> SEQ ID NO 38
<211> LENGTH: 369
<212> TYPE: DNA
<213> ORGANISM: Artificial Sequence
<220> FEATURE:
<223> OTHER INFORMATION: synthetically constructed MAB297 heavy chain
      variable domain nucleotide sequence

<400> SEQUENCE: 38
caggtgcaac tggtgcagtc tggggaggc gtggtccagc ctgggaggtc cctgagactc      60
tcctgttcag cctctggatt caccttcagc aactataata tgcactgggt ccgccaggct    120
ccaggcaagg ggccggagtg ggtggcagtt atatcaaaag atggaaacga aaaacactat    180
gcagagtctg cgaagggccg attcaccatc tccagagaca attccaagaa cacgctgtat    240
atggaaatgc acagcctgac acctgaggac acggctatgt attactgtac gagagatggg    300
cgaaccgatg gtactgggta ctccggtatt cttgatatct ggggccaagg acaaaggtc     360 atcgtctct                                                            369

<210> SEQ ID NO 39
<211> LENGTH: 370
<212> TYPE: DNA
<213> ORGANISM: Artificial Sequence
<220> FEATURE:
<223> OTHER INFORMATION: synthetically constructed MAB309 and MAB318
      heavy chain variable domain nucleotide sequence

<400> SEQUENCE: 39
caggtgcagc tggtgcagtc tggggaggc gtggtccagc ctgggacgtc cctgagactc      60
tcctgtgcag cctctggatt catgttcaat acctataata tgcactgggt ccgccaggct    120
ccaggcaagg ggctggagtg ggtggcagtt atatcaaatg atggaaccta taagcatttc    180
gctgactccc tgaagggccg attcagcatc tccagagacg attccaagaa cacgctgtat    240
ctgcacatga acagcctgag acctgacgac acggctatat attactgtgc gagagatggc    300
cgtagtgttg gcgggtttag tgggatcctc gacccctggg gccagggaac cctggtcacc    360
gtctcctcag                                                           370

<210> SEQ ID NO 40
<211> LENGTH: 370
<212> TYPE: DNA
<213> ORGANISM: Artificial Sequence
<220> FEATURE:
<223> OTHER INFORMATION: synthetically constructed MAB310 heavy chain
      variable domain nucleotide sequence

<400> SEQUENCE: 40
caggtgcagc tggtgcagtc tggggaggc gtggtccagc ctgggacgtc cctgagactc      60
tcctgtgcag cctctggatt catgttcaat acctacaata tgcactgggt ccgccaggct    120
ccaggcaagg ggctggagtg ggtggcagtt atatcaaatg atggaaccta taagtactcc    180
gctgactccc tgaagggccg attcagcatc tccagagaca attccaagaa cacgttgtat    240
ctgcacatga acagcctgag acctgacgac acggctgtat attactgtgc gagagatggc    300
cgtagtgttg gcgggtttag tgggatcctc gacccctggg gccagggaac cctggtcacc    360
gtctcctcag                                                           370

<210> SEQ ID NO 41
<211> LENGTH: 370
<212> TYPE: DNA
<213> ORGANISM: Artificial Sequence
<220> FEATURE:
<223> OTHER INFORMATION: synthetically constructed MAB313 heavy chain
      variable domain nucleotide sequence

<400> SEQUENCE: 41

```
caggtgcagc tggtgcagtc tgggggaggc gtgatccagc ctggagggtc cctgacactc      60
tcctgtgcag cctctggatt caccttcagt gcctattctc tacactgggt ccgccaggct     120
ccaggcaaag ggctacagtg ggtggcggtt atctcatttg atgggaattt taaacacttc     180
gcagactccc tgaggggccg attcaccatc tccagagaca attccaagaa cagattctat     240
ttgcaaatga atggcctgag aggtgaggac acggctgtat attactgtgc gagagatgga     300
cgtgctgttg acgggtttag tgggatcctc gacttctggg gccagggaac cctagtcagc     360
gtctcctcag                                                             370
```

<210> SEQ ID NO 42
<211> LENGTH: 370
<212> TYPE: DNA
<213> ORGANISM: Artificial Sequence
<220> FEATURE:
<223> OTHER INFORMATION: synthetically constructed MAB314 heavy chain
      variable domain nucleotide sequence

<400> SEQUENCE: 42

```
caggtgcagc tgcaggagtc ggggggaggc ttggtccagc cggggggtc cctgaaactc       60
tcctgtgcag tctctggatt ctccttcggt ggctctgcaa tgcactgggt ccgccaggct     120
tccgggaaag ggctggagtg gattggccat attagaagcg gagctaataa tttcgagaca     180
gcatatgctc cgtcgctgga tggcaggttc accatctcca gagacgattc aaagaacacg     240
gcgtatctgc acatgaacag cctgaaaacc gatgacacgg ccatgtattt ctgcactacc     300
ggacttatag cgtcaggtga tgcaaatttt gactactggg gccagggaac ccaggtcacc     360
gtctcctcgg                                                             370
```

<210> SEQ ID NO 43
<211> LENGTH: 370
<212> TYPE: DNA
<213> ORGANISM: Artificial Sequence
<220> FEATURE:
<223> OTHER INFORMATION: synthetically constructed MAB316 heavy chain
      variable domain nucleotide sequence

<400> SEQUENCE: 43

```
caggtgcagc tggtgcagtc tgggggaggc gtggtccagc ctggagggtc cctgacactc      60
tcctgtgcag cctctggatt caccttcagt ggcttttctc tacactgggt ccgccaggct     120
ccaggcaagg ggctacagtg ggtggcggtt atctcatttg atgggaacca taaacacttc     180
gcagactccc tgaagggccg attcaccatc tccagagaca attccaagaa cacattgtat     240
ttgcaaatta atgacctgag aggtgaggac acggctgtat attactgtgc gagagatgga     300
cgtgctgttg acgggtttag tgggattctc gacttctggg gccagggaac cctggtcagc     360
gtctcctcag                                                             370
```

<210> SEQ ID NO 44
<211> LENGTH: 370
<212> TYPE: DNA

<213> ORGANISM: Artificial Sequence
<220> FEATURE:
<223> OTHER INFORMATION: synthetically constructed MAB319 heavy chain
      variable domain nucleotide sequence

<400> SEQUENCE: 44

```
caggtgcagc tggtggagtc tgggggaggc gtggtccagc ctggagggtc cctgagactc    60
tcctgttcag cctcaggatt caccttcagt gactataatc tacactgggt ccgccaggct   120
ccaggcaagg ggctggagtg ggtggcagtc atctcaattg atggaagcga taaacaccac   180
gcagactccg tgaagggccg attcaccgtc tccagagaca attccaagaa cacagtgagt   240
ctacaaatgg acagcctgag acctgaagac acggctgtat attactgtgc gagagatggc   300
cgtagtgtgg gcggctacag tgggatcctc gaccctggg gccagggaac cctggtcacc   360
gtctcctcag                                                          370
```

<210> SEQ ID NO 45
<211> LENGTH: 383
<212> TYPE: DNA
<213> ORGANISM: Artificial Sequence
<220> FEATURE:
<223> OTHER INFORMATION: synthetically constructed MAB321 heavy chain
      variable domain nucleotide sequence

<400> SEQUENCE: 45

```
gaggtgcagc tggtggagtc cggagcagag gtgaaaaagc ccggggagtc tctgaagatc    60
tcctgtcagg gttctggata caggtttacc aattactgga tcgcctgggt gcgccagatg   120
cccgggaaag gcctggagtg gatggggatc atctatcctg gtgactctga taccagatat   180
cacccgtcct tccaaggcca ggtcaccatc tcatccgaca atccctcaa caccgcctac   240
ctgcagtgga gcagcctgaa gcctcggac accgccgtgt attactgtgc gagacaccac   300
tgccttagta ccaactgcca aaccgcagtg gctggatata tgactactg gggccaggga   360
aaccctggtc gccgtctcct cag                                           383
```

<210> SEQ ID NO 46
<211> LENGTH: 372
<212> TYPE: DNA
<213> ORGANISM: Artificial Sequence
<220> FEATURE:
<223> OTHER INFORMATION: synthetically constructed MAB322 heavy chain
      variable domain nucleotide sequence

<400> SEQUENCE: 46

```
caggtgcagc tggtggagtc cggggggggc gtggtccagc ctggagggtc cctgagactt    60
tcctgttcag cctctggatt caccttcacc aactataaca tgcactgggt ccgccaggct   120
ccaggcaagg ggctggagtg ggtggcagtt acgtcaaaag atggaaacga aaacactttt   180
gcagactccg tgaagggccg attcaccatc tccagagaca attccaagaa cacgctgtat   240
ctggaaatga acaccctgac agctgaggac acggcgatat attactgtac gagagatggg   300
cgaaccgatg gtactgggta ctccggtatt cttgatatct ggggccaagg gacaaaggtc   360
accgtctcct ca                                                       372
```

<210> SEQ ID NO 47
<211> LENGTH: 372
<212> TYPE: DNA
<213> ORGANISM: Artificial Sequence
<220> FEATURE:
<223> OTHER INFORMATION: synthetically constructed MAB323 heavy chain
      variable domain nucleotide sequence

<400> SEQUENCE: 47

```
caggtgcagc tggtgcagtc tgggggaggg gtggtccagc ctggaggtc cctgagactc      60 tcctgtgcag cctctggatt caccttcagt aactttgcta tgcactgggt ccgccaggct    120
ccaggcaagg ggctggagtg ggtggcagtt atatcaaatg ctggaaggga aacacactac    180
gcagactccg tgaagggccg attcaccgtc tccagagaca attccaagaa tatgttgtct    240
ctgcaaatga acagcctgag aggtgaggac acggctgtgt attactgtgc gagagatggg    300
cgaaccgatg gtagtggcta ttccggtgtt cttgatatct gggcccaagg gacactggtc    360
actgtctcct ca                                                         372
```

<210> SEQ ID NO 48
<211> LENGTH: 369
<212> TYPE: DNA
<213> ORGANISM: Artificial Sequence
<220> FEATURE:
<223> OTHER INFORMATION: synthetically constructed MAB338 heavy chain
      variable domain nucleotide sequence

<400> SEQUENCE: 48

```
caggtgcagc tggtggagtc cggggggaggc gtggtccagc ctggaggtc cctgagactc     60 tcctgttcag gctctggatt caccttcagt gactataatc tacactgggt ccgccaggct   120
ccaggcaagg ggctggaatg ggtggcagtc atttcaattg atggaactaa taaacaccac   180
gcagactccg tgaagggccg attcaccatc tccagagaca actccaagaa tacagtgaat   240
ctggaaatga gtcggctgaa agcagaagac acggctgtat attactgtgt gagagatggg   300
cgaagtattg gcggctacag tggaatcttc gaccctggg gccagggaac cctggtcacc   360
gtctcctca                                                           369
```

<210> SEQ ID NO 49
<211> LENGTH: 369
<212> TYPE: DNA
<213> ORGANISM: Artificial Sequence
<220> FEATURE:
<223> OTHER INFORMATION: synthetically constructed MAB343 heavy chain
      variable domain nucleotide sequence

<400> SEQUENCE: 49

```
caggtgcagc tgcaggagtc aggggggaggc gtggtccagc ctggaggtc cctgagactc     60 tcctgtgcag cctctggatt caccttcaat acctacaata tgcactgggt ccgccaggct   120
ccaggcaagg ggctggagtg ggtggcagtt atatcaaatg atggaaccta taaatactcc   180
gctgactccg tgaagggccg attcagcatc tccagaggca attccaagaa cacgttgtat   240
ctgcagatga acagcctgag acctgacgac acggctgtat attactgtgc gagagatggg   300
cgtagtgttg gcgggtttag tgggatcctc gaccctggg gccagggaac cctggccacc   360
gtctcctca                                                           369
```

<210> SEQ ID NO 50
<211> LENGTH: 370
<212> TYPE: DNA
<213> ORGANISM: Artificial Sequence
<220> FEATURE:
<223> OTHER INFORMATION: synthetically constructed MAB345 heavy chain
      variable domain nucleotide sequence

<400> SEQUENCE: 50

```
caggtgcagc tggtggagtc cggggggaggc gtggtccagc ctggaggtc cctgagactc     60
```

```
tcctgtgcag cctctggatt caccttcagt gactacaata tgcactgggt ccgccaggct      120
ccaggcaagg gctggagtg gtggcagtt atttcaattg atggaacgta taaatactcc       180
gctgactccg tggcgggccg attcagtctc tccagagaca attccaagaa cacgttgtat     240
ttgcagatga atagtctgag acctgacgac acggctatat attattgcgc gagagatggg    300
cgtagtgttg cgggtttag tgggatcctc gaccctgggg ccagggaac cctggtcacc      360 gtctcctcag                                                            370

<210> SEQ ID NO 51
<211> LENGTH: 321
<212> TYPE: DNA
<213> ORGANISM: Homo sapiens
<220> FEATURE:
<221> NAME/KEY: misc_feature
<222> LOCATION: (1)...(321)
<223> OTHER INFORMATION: light chain nucleotide sequence of constant
      kappa region

<400> SEQUENCE: 51
actgtggctg caccatctgt cttcatcttc ccgccatctg atgagcagtt gaaatctgga     60
actgctagcg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                               321

<210> SEQ ID NO 52
<211> LENGTH: 327
<212> TYPE: DNA
<213> ORGANISM: Artificial Sequence
<220> FEATURE:
<223> OTHER INFORMATION: synthetically constructed MAB297 and MAB322
      light chain variable domain nucleotide sequence

<400> SEQUENCE: 52
gaaattgtaa tgacgcagtc tccagccacc ctgtctttgt ctccagggga aagagccacc    60
ctctcctgca gggccagtca gagtgttggc ggctacttag cctggtacca acagaaacct   120
gaccaggctc ccaggctcct catctatgat gtttccaata gggccgctgg catcccagcc   180
aggttcagtg gcagtgggtc tgggacagac ttcactctca ccatcagcag cctggagcct   240
gaagattttg cagtttatta ctgtcagcag cggaacacct ggcctccgct cactttcggc   300
ggagggacca aggtggagat caaacga                                        327

<210> SEQ ID NO 53
<211> LENGTH: 327
<212> TYPE: DNA
<213> ORGANISM: Artificial Sequence
<220> FEATURE:
<223> OTHER INFORMATION: synthetically constructed MAB309 light chain
      variable domain nucleotide sequence

<400> SEQUENCE: 53
gaaattgtgt tgacgcagtc tccagccacc ctgtctttgt ctccagggga tagagccacc    60
ctctcctgca gggccagtca gactgttggc aggtacttag cctggtacca acaaaaacct   120
ggccaggctc ccaggctcct catctatgat gcttccgaca gggccactgg catctcagcc   180
aggttcagtg gcagtgggtc tgggacagat ttcactctca ccatcagcag cctggagcct   240
```

```
gaagattttg cagtctatta ctgtcagcag cggagcagct ggccgccgct cactttcggc    300
ggagggacca aggtggagat caaacga                                        327
```

<210> SEQ ID NO 54
<211> LENGTH: 327
<212> TYPE: DNA
<213> ORGANISM: Artificial Sequence
<220> FEATURE:
<223> OTHER INFORMATION: synthetically constructed MAB310 light chain
      variable domain nucleotide sequence

<400> SEQUENCE: 54

```
gaaattgtgt tgactcagtc tccagccacc ctgtctttgt ctccagggga tagagccacc     60
ctctcctgca gggccagtca gactgttggc aggtacttag cctggtacca acagaaacct    120
ggccaggctc ccaggctcct catctatgat gcttccgaca gggccactgg catctcagcc    180
aggttcagtg gcagtgggtc tgggacagat ttcactctca ccatcagcag cctagagcct    240
gaagattttg cagtctatta ctgtcagcag cggagcaact ggcctccgct cactttcggc    300
ggagggacca aggtggagat caaacga                                        327
```

<210> SEQ ID NO 55
<211> LENGTH: 327
<212> TYPE: DNA
<213> ORGANISM: Artificial Sequence
<220> FEATURE:
<223> OTHER INFORMATION: synthetically constructed MAB313 light chain
      variable domain nucleotide sequence

<400> SEQUENCE: 55

```
gaaattgtga tgactcagtc tccagccacc ctgtctttgt ctccagggga aagagccacc     60
ctctcctgca gggccagtca gagtgttggc agatacttaa cttggttcca gcagaaacct    120
ggccaggctc ccaggctcct catctatgat gcttccgaga gggccactgg catcccagcc    180
aggttcagtg gcagtgggtc tgggacagac ttcactctca ccatcagcag cctagagcct    240
gaagattttg cagtttatta ctgtcaacag cgtgctaact ggcctccgct cactttcggc    300
ggagggacca aggtggagat caaacga                                        327
```

<210> SEQ ID NO 56
<211> LENGTH: 327
<212> TYPE: DNA
<213> ORGANISM: Artificial Sequence
<220> FEATURE:
<223> OTHER INFORMATION: synthetically constructed MAB314 light chain
      variable domain nucleotide sequence

<400> SEQUENCE: 56

```
gaaattgtga tgacccagtc tccaggcacc ctgtccttgt ttccagggga aagagccacc     60
ctctcctgca gggccagtca gactgttagg aacggctact tagcctggta ccagcagaaa    120
cctggccagg ctcccaggct cctcatctat ggtgcttcca tcaggccac tggcatccca    180 gacaggttca gtggcagtgg gtctgagaca gacttcaccc tcagcatcac cagagtggag    240
cctgaagatt ttgcagttta ttactgtcaa cagtatggaa ggttatcgtc acttttggc    300 cagggggacca agctggacct caaacga                                       327
```

<210> SEQ ID NO 57
<211> LENGTH: 325
<212> TYPE: DNA
<213> ORGANISM: Artificial Sequence
<220> FEATURE:
<223> OTHER INFORMATION: synthetically constructed MAB316 light chain
      variable domain nucleotide sequence

<400> SEQUENCE: 57
gaaattgtga tgacccagtc tccagccacc ctgtctttgt ctccagggga aagagccacc      60
ctctcctgca gggccagtca gagtgttggc agatacttaa cttggttcca gcagaaacct    120
ggccaggctc ccaggctcct catctatgat gcttccgaga gggccactgg cgtcccagcc    180
aggttcagtg gcagtgggtc tgggacagac ttcactctca ccatcagcag cctagagcct    240
gaagattttg cagtttatta ctgtcaacag cgtagtaact ggcctccgct cactttcggc    300
ggagggacca aggtggagat caaac                                           325

<210> SEQ ID NO 58
<211> LENGTH: 325
<212> TYPE: DNA
<213> ORGANISM: Artificial Sequence
<220> FEATURE:
<223> OTHER INFORMATION: synthetically constructed MAB318 light chain
      variable domain nucleotide sequence

<400> SEQUENCE: 58
gaagttgtgc tgacgcagtc tccagccacc ctgtctttgt ctccagggga tagagccacc     60
ctctcctgca gggccagtca gactgttggc aggtacttag cctggtacca acaaaaacct   120
ggccaggctc ccaggctcct catctatgat gcttccgaca gggccactgg catctcagcc   180
aggttcagtg gcagtgggtc tgggacagat ttcactctca ccatcggcag cctggagcct   240
gaagattttg cagtctatta ctgtcagcag cggagcagct ggccgccgct cactttcggc   300
ggagggacca aggtggagat caaac                                          325

<210> SEQ ID NO 59
<211> LENGTH: 325
<212> TYPE: DNA
<213> ORGANISM: Artificial Sequence
<220> FEATURE:
<223> OTHER INFORMATION: synthetically constructed MAB319 light chain
      variable domain nucleotide sequence

<400> SEQUENCE: 59
gaaattgtgt tgacgcagtc tccagccacc ctgtctttgt ctccagggga aagggccacc     60
ctctcctgca gggccagtca gagtgttggc agctacttag cctggtatca acagaaacct   120
ggccaggctc ccaggctcct catctatgat gcatccgaga gggccactgg catcccagcc   180
aggttcagtg gcagtgggtc tgggacagac ttcactctca ccatcagcag cctagagcct   240
gaagatgttg cagtttatta ctgtcagcag cgtaacaact ggcctccgct caccttcggc   300
ggagggacca aggtggagat caaac                                          325

<210> SEQ ID NO 60
<211> LENGTH: 339
<212> TYPE: DNA
<213> ORGANISM: Artificial Sequence
<220> FEATURE:
<223> OTHER INFORMATION: synthetically constructed MAB321 light chain
      variable domain nucleotide sequence

<400> SEQUENCE: 60
gaaattgtga tgacccagtc tccagactcc cttgctgtgt ctctgggcga gagggccacc     60
atcaactgca agtccagtca gagtattttta ttcagctcca gaatcagaa ccacttagct   120

```
tggtaccagc agaaaccagg acagcctcct aagctgctga tttactgggc atctacccgg      180
gaatccgggg tccccgaccg attcagtggc agcgggtctg ggacagattt cactctcacc      240
atcagcagcc tccaggctga agatgtggca gtttattact gtcagcaata ttataatatt      300
cctcacactt tcggcggagg gaccaaggtg gagatcaaa                             339
```

<210> SEQ ID NO 61
<211> LENGTH: 321
<212> TYPE: DNA
<213> ORGANISM: Artificial Sequence
<220> FEATURE:
<223> OTHER INFORMATION: synthetically constructed MAB323 light chain
      variable domain nucleotide sequence

<400> SEQUENCE: 61

```
gaaattgtgt tgactcagtc tccagccacc ttgtctttgt ctccagggga aagagccacc       60
ctctcctgcc gggccagtca gagtgttaac cgctacttag cctggttcca acacagacct      120
ggccagcctc ccaggctcct catctatgat gcgtccaaga gggccactgg catcccagcc      180
aggttcagtg gcagtgggtc tgggacagac ttcactctca ccatcagcag cctagagcct      240
gaagattttg cagtttatta ctgtcagcag cgtagcaact ggccgctcac tttcggcgga      300
gggaccaagg tggagatcaa g                                                321
```

<210> SEQ ID NO 62
<211> LENGTH: 324
<212> TYPE: DNA
<213> ORGANISM: Artificial Sequence
<220> FEATURE:
<223> OTHER INFORMATION: synthetically constructed MAB338 light chain
      variable domain nucleotide sequence

<400> SEQUENCE: 62

```
gaaattgtgt tgacccagtc tccagccacc ctgtctttgt ctccagggga aagagccacc       60
ctctcctgca gggccagtca gagtgttgac aggtacttag cctggtacca acagaaacct      120
ggccaggctc ccagactcct catctatgat gcatcccaga gggccactgg catcccagcc      180
aggttcagtg gcagtgggtc cgggacagac ttcactctcg ccatcagcag cctggagcct      240
gaagatgttg cagtttatta ctgtcagcag cgtagtaact ggcctccgct caccttcggc      300
ggagggacca aatagagat caaa                                              324
```

<210> SEQ ID NO 63
<211> LENGTH: 325
<212> TYPE: DNA
<213> ORGANISM: Artificial Sequence
<220> FEATURE:
<223> OTHER INFORMATION: synthetically constructed MAB343 light chain
      variable domain nucleotide sequence

<400> SEQUENCE: 63

```
gaaatcgtga tgacccagtc tccagccacc ctgtctttgt ctccagggga tagagccacc       60
ctctcctgca gggccagtca gagtgttggc agctacttag cctggtacca acagaaacct      120
ggccaggctc ccaggctcct catctatgat gcttccgaca gggccactgg catcccagcc      180
aggttcagtg gcagtgggtc tgggacagat ttcactctca ccatcagcag cctagagcct      240
gaagattttg cagtttatta ctgtcagcag cgtagcaact ggcctccgct cactttcggc      300
ggagggacca aggtggagat caaac                                            325
```

<210> SEQ ID NO 64

| | |
|---|---|
| <211> LENGTH: 324 | |
| <212> TYPE: DNA | |
| <213> ORGANISM: Artificial Sequence | |
| <220> FEATURE: | |
| <223> OTHER INFORMATION: synthetically constructed MAB345 light chain variable domain nucleotide sequence | |

<400> SEQUENCE: 64

```
gaaattgtga tgacccagtc tccagccacc ctgtctttgt ctccagggga tagagccacc    60
ctctcctgca gggccagtca gagtgttggc agctacttag cctggtacca acagaaacct   120
ggccaggctc ccaggctcct catgtatgat tcttccgtca gggccactgg catcccagcc   180
aggttcagtg gcagcgggtc tgggacagat ttcactctca ccatcagcag cctagagcct   240
gaagattttg cagtttatta ctgtcagcag cgtaacaact ggcctccgct cactttcggc   300
ggagggacca aggtggagat caaa                                          324
```

<210> SEQ ID NO 65
<211> LENGTH: 321
<212> TYPE: DNA
<213> ORGANISM: Homo sapiens
<220> FEATURE:
<221> NAME/KEY: misc_feature
<222> LOCATION: (1)...(321)
<223> OTHER INFORMATION: light chain nucleotide sequence of constant kappa region

<400> SEQUENCE: 65

```
actgtggctg caccatctgt cttcatcttc ccgccatctg atgagcagtt gaaatctgga    60
actgctagcg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321
```

<210> SEQ ID NO 66
<211> LENGTH: 318
<212> TYPE: DNA
<213> ORGANISM: Homo sapiens
<220> FEATURE:
<221> NAME/KEY: misc_feature
<222> LOCATION: (1)...(318)
<223> OTHER INFORMATION: light chain nucleotide sequence of constant lambda region

<400> SEQUENCE: 66

```
ggtcagccca aggctgcccc ctctgtcact ctgttcccgc cctctagcga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac ccctccaaa    180
caaagcaaca caagtacgc ggccagcagc tatctgagcc tgacgcctga gcagtggaag   240
tcccacagaa gctacagctg ccaggtcacg catgaaggga gcaccgtgga agacagtg     300
gtccctgcag aatgctct                                                 318
```

<210> SEQ ID NO 67
<211> LENGTH: 8
<212> TYPE: PRT
<213> ORGANISM: Artificial Sequence
<220> FEATURE:
<223> OTHER INFORMATION: synthetically constructed CDR1 region of 4A2 heavy chain VH3-30

```
<400> SEQUENCE: 67

Gly Phe Thr Phe Asn Arg His Gly
1               5

<210> SEQ ID NO 68
<211> LENGTH: 9
<212> TYPE: PRT
<213> ORGANISM: Artificial Sequence
<220> FEATURE:
<223> OTHER INFORMATION: synthetically constructed CDR1 region of 19B10
      heavy chain VH4-31 D2 J6

<400> SEQUENCE: 68

Gly Ser Ile Ser Ser Glu Asp Phe Cys
1               5

<210> SEQ ID NO 69
<211> LENGTH: 7
<212> TYPE: PRT
<213> ORGANISM: Artificial Sequence
<220> FEATURE:
<223> OTHER INFORMATION: synthetically constructed CDR2 region of 4A2
      heavy chain VH- 30

<400> SEQUENCE: 69

Ser Ser Asp Gly Ala Asn Gln
1               5

<210> SEQ ID NO 70
<211> LENGTH: 6
<212> TYPE: PRT
<213> ORGANISM: Artificial Sequence
<220> FEATURE:
<223> OTHER INFORMATION: synthetically constructed CDR2 region of 19B10
      heavy chain VH4-31 D2 J6

<400> SEQUENCE: 70

Ile Cys Tyr Thr Gly Asp
1               5

<210> SEQ ID NO 71
<211> LENGTH: 18
<212> TYPE: PRT
<213> ORGANISM: Artificial Sequence
<220> FEATURE:
<223> OTHER INFORMATION: synthetically constructed CDR3 region of 4A2
      heavy chain VH3-30

<400> SEQUENCE: 71

Ala Arg Asp Gly Arg Cys Glu Gly Glu Arg Cys Tyr Ser Gly Val Thr
1               5                   10                  15

Asp Phe

<210> SEQ ID NO 72
<211> LENGTH: 20
<212> TYPE: PRT
<213> ORGANISM: Artificial Sequence
<220> FEATURE:
<223> OTHER INFORMATION: synthetically constructed CDR3 region of 19B10
      heavy chain VH4-31 D2 J6

<400> SEQUENCE: 72

Ala Arg Glu Asp Arg Arg Gln Leu His Ser Arg Pro Tyr Phe Tyr Tyr
1               5                   10                  15

Gly Leu Asp Val
```

-continued

```
                20

<210> SEQ ID NO 73
<211> LENGTH: 6
<212> TYPE: PRT
<213> ORGANISM: Artificial Sequence
<220> FEATURE:
<223> OTHER INFORMATION: synthetically constructed CDR1 region of 4A2
      light chain L6 IgKV3-11

<400> SEQUENCE: 73

Gln Asn Ile Gly Gly Tyr
1               5

<210> SEQ ID NO 74
<211> LENGTH: 11
<212> TYPE: PRT
<213> ORGANISM: Artificial Sequence
<220> FEATURE:
<223> OTHER INFORMATION: synthetically constructed CDR1 region of 19B10
      light chain A3 IgKV2

<400> SEQUENCE: 74

Gln Ser Leu Leu His Ser Asn Gly His Asn Tyr
1               5                   10

<210> SEQ ID NO 75
<211> LENGTH: 3
<212> TYPE: PRT
<213> ORGANISM: Artificial Sequence
<220> FEATURE:
<223> OTHER INFORMATION: synthetically constructed CDR2 region of 4A2
      light chain L6 IgKV3-11

<400> SEQUENCE: 75

Asp Ala Ser
1

<210> SEQ ID NO 76
<211> LENGTH: 2
<212> TYPE: PRT
<213> ORGANISM: Artificial Sequence
<220> FEATURE:
<223> OTHER INFORMATION: synthetically constructed CDR2 region of 19B10
      light chain A3 IgKV2

<400> SEQUENCE: 76

Leu Gly
1

<210> SEQ ID NO 77
<211> LENGTH: 10
<212> TYPE: PRT
<213> ORGANISM: Artificial Sequence
<220> FEATURE:
<223> OTHER INFORMATION: synthetically constructed CDR3 region of 4A2
      light chain L6 IgKV3-11

<400> SEQUENCE: 77

Gln Gln Arg Asn Ser Trp Pro Pro Leu Thr
1               5                   10

<210> SEQ ID NO 78
<211> LENGTH: 8
<212> TYPE: PRT
<213> ORGANISM: Artificial Sequence
<220> FEATURE:
<223> OTHER INFORMATION: synthetically constructed CDR3 region of 19B10
``` light chain A3 IgKV2

<400> SEQUENCE: 78

Gln Ala Leu Gln Thr Pro Asn Thr
1               5

<210> SEQ ID NO 79
<211> LENGTH: 14
<212> TYPE: PRT
<213> ORGANISM: Artificial Sequence
<220> FEATURE:
<223> OTHER INFORMATION: synthetically contstructed AD-2 amino acid
      sequence

<400> SEQUENCE: 79

Asn Glu Thr Ile Tyr Asn Thr Thr Leu Lys Tyr Gly Asp Val
1               5                   10

HIGH AFFINITY HUMAN ANTIBODIES TO HUMAN CYTOMEGALOVIRUS (CMV) GB PROTEIN

CROSS-REFERENCE TO RELATED APPLICATIONS

This application is a divisional of U.S. Ser. No. 13/162,497, filed Jun. 16, 2011, now allowed, which claims priority from U.S. provisional application 61/355,499 filed Jun. 16, 2010. The contents of these applications are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 388512012710SeqList.txt, date recorded: Apr. 27, 2015, size: 71,287 bytes).

TECHNICAL FIELD

The invention relates to human monoclonal antibodies (mAbs) against the gB protein of CMV, for therapeutic and prophylactic use to prevent or ameliorate the effects on the fetus of CMV infection during pregnancy, and to treat CMV infection in immunocompromised patients, including transplant patients.

BACKGROUND ART

CMV is a major disease-causing agent in transplant patients, other immunocompromised patients, and newborns. About 40,000 infants are born shedding CMV every year in the US. Of these, 8,000 are born with symptoms and/or severe handicaps and up to 8,000 more will later develop progressive hearing loss. About half of pregnant mothers have adequate immunity naturally. Thus it is known that effective mAbs exist in human blood. This is also shown by successful passive transfer of immunity by intravenously administered gamma globulin (IVIG), which has shown very high efficacy for protecting the fetus. This is in contrast to the limited efficacy observed for IVIG in the transplant setting, for which cellular immunity is apparently more important than humoral immunity.

A substantial portion of the natural response to CMV is directed towards the gB protein (Park, J. W., et al., *J. Korean Med. Sci.* (2000) 15:133-138). The Towne vaccine is an attenuated live virus vaccine passaged extensively in vitro, which induces antibodies that neutralize fibroblast infection, but not endothelial cell infection. This vaccine is known to be safe and has been studied for 20 years (Adler, S. P., et al., *Pediatr. Infect. Dis. J.* (1998) 17:200-206). Blood donors useful for isolating antibodies to gB as described below include seropositive individuals with previous exposure to CMV and seronegative subjects before and after vaccination with the Towne vaccine.

Antibodies to gB protein of CMV have been prepared (Nozawa N., et al., *J. Clin. Virol.* (2009) [Epub ahead of print], Nakajima, N., et al. (U.S. 2009/0004198 A1), Lanzavecchia, A, et al. (U.S. 2009/0004198 A1), Ohlin, M., et al. (*J. Virol.* (1993) 67:703-710). A neutralizing antibody to the AD-2 domain of gB, ITC88, has been reported (Lantto, *Virology* (2003) 305:201-209). However, prior efforts to clone human antibodies against CMV, while successful, are limited in scope and no high affinity (sub-nanomolar) antibodies have been described. High affinity is a key parameter as weak affinity antibodies to CMV actually promote transmission across the human placenta (Nozawa, supra), an aspect of the pathology not seen in rodents. Human CMV has a double stranded DNA genome of approximately 236 kb and is a prototypical member of the β-herpesvirus family. The high complexity of the genome means that there are many potential antigens of interest. Efforts to characterize neutralizing antibodies and their associated epitopes resulted in a subunit vaccine based on glycoprotein B (gB) that elicits an effective neutralizing response, but, when tested in a cohort of seronegative women has only 50% efficacy. This appears to be the highest efficacy of any CMV vaccine. Since vaccines typically induce antibodies with a range of affinities, the disappointing efficacy of the tested vaccines to date may be attributable to the requirement for high affinity antibodies, which argues in favor of supplying a high affinity mAb directly as a prophylactic strategy.

Failure to focus the immune response on the specific neutralizing epitopes has also been postulated as the cause of the poor efficacy (Marshall, B. C., et al., *Viral. Immunol.* (2003) 16:491-500. Another suspected technical problem in developing anti-CMV vaccines is that they have only been assessed for their ability to generate antibodies that neutralize fibroblast infection although infection of other cell types has increasingly become a focus for understanding the viral pathology. This bias reflects technical obstacles with regard to growth of the virus in vitro. Repeated virus passage on fibroblast cells is believed to have caused many lab strains to lose tropism for endothelial and epithelial cells. During the last few years, this deficit has been associated with the loss of one or more components of the gH/gL/UL131-UL128 glycoprotein complex on the virus surface.

Clearly a need exists for a more effective anti-CMV prophylaxis strategy.

DISCLOSURE OF THE INVENTION

Human antibodies that are specifically immunoreactive with the CMV gB protein, with improved affinity compared to prior antibodies (human or murine) and with neutralizing ability have been prepared. The humoral immune system is capable of producing millions of antibody structures with tens of thousands of well differentiated binding capabilities, yet the protective antibodies are only a very small subset of these. The present inventors have employed CellSpot™ technology (Harriman, W. D., et al., *J. Immunol. Methods* (2009) 34:135-145, Collarini, E. J., et al., *J. Immunol.* (2009) 183:6338-6345), and U.S. Pat. No. 7,413,868), all incorporated herein by reference, to generate a panel of mAbs from blood of donors verified as having high titer to CMV.

Thus, in one aspect, the invention is directed to human monoclonal antibodies or immunoreactive fragments thereof that bind an epitope on the gB protein, with a preferred embodiment being binding to a conserved sequence therein. These antibodies display neutralizing capabilities in standard plaque forming assays for neutralization of CMV and demonstrate $EC_{50}$ in such assays of <500 ng/ml, preferably <200 ng/ml, more preferably <100 ng/ml. The antibodies of the invention also have affinities for the gB protein of CMV strain AD169 of <10 nM or <5 nM or <1 nM.

For use in the methods of the invention to treat CMV infection or to enhance resistance to CMV, the monoclonal antibodies or fragments of the invention may be immunoreactive with a multiplicity of CMV strains and a single monoclonal antibody may suffice to have the desired effect.

Alternatively, the subject to be treated or to be made resistant may be administered more than a single monoclonal antibody, which bind to the same or different CMV proteins.

The invention also includes pharmaceutical compositions useful for prophylaxis or treatment which contain as an active agent a single antibody or immunoreactive fragment of the invention, or no more than two antibodies or fragments of the invention.

Other aspects of the invention include methods of using the antibodies to treat CMV in human subjects or to induce resistance to infection in human subjects.

The monoclonal antibodies of the invention may be produced recombinantly and therefore the invention also includes recombinant materials for such production as well as cell lines or immortalized cells and non-human multicellular organisms or cells thereof, or microbial cells, for the production of these antibodies. In one embodiment, cells obtained from human subjects are produced in "immortalized" form wherein they have been modified to permit secretion of the antibodies for a sufficient time period that they may be characterized and the relevant encoding sequence cloned.

Figure 1:
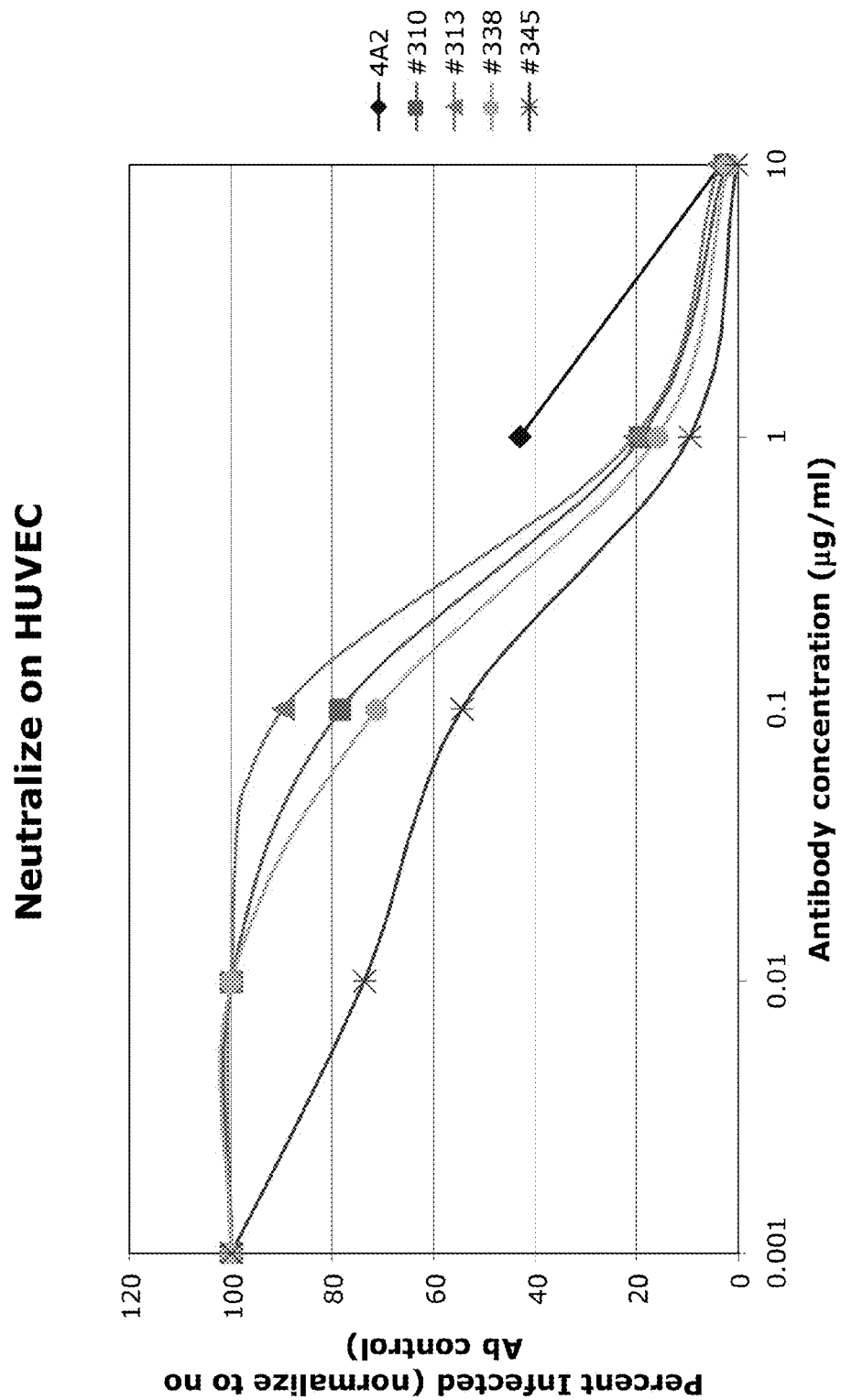
FIG. 1 shows the neutralization of VR1814 by mAbs 4A2, 310, 313, 338, and 345 in HUVECs.

MODES OF CARRYING OU include nutritional substances such as vitamins, or any other beneficial compound other than an antibody.

In one embodiment, when the formulations for administration are used in order to increase resistance to infection, complete antibodies, including the complement-containing Fc region are employed. Typically, the antibodies are administered as dosage levels of 0.01-20 mg/kg of human subjects or in amounts in the range of 0.01-5 mg/kg or intermediate amounts within these ranges. In one embodiment, amounts in the range of 0.1-1.0 mg/kg are employed. Repeated administration separated by several days or several weeks or several months may be beneficial.

In another embodiment, for a therapeutic effect in order to reduce viral load, complete antibodies, containing the complement-containing Fc region are also employed. The amounts administered in such protocols are of the order of 0.001-50 mg/kg or intermediate values in this range such as 0.01, 1 or 10 mg/kg are employed. Repeated administration may also be used. The therapeutic treatment is administered as soon as possible after diagnosis of infection, although administration within a few days is also within the scope of the invention. Repeated administration may also be employed. In order to reduce the inflammatory response in the lungs, only the immunospecific fragments of the antibodies need be employed. Dosage levels are similar to those for whole antibodies. Administration of mixtures of immunospecific fragments and entire antibodies is also included within the scope of the invention.

Administration of the antibody compositions of the invention is typically by injection, generally intravenous injection. Thus, parenteral administration is preferred. However, any workable mode of administration is included, including gene therapy (production of recombinant antibody in vivo).

The formulations are prepared in ways generally known in the art for administering antibody compositions. Suitable formulations may be found in standard formularies, such as *Remington's Pharmaceutical Sciences*, latest edition, Mack Publishing Co., Easton, Pa., incorporated herein by reference. The formulations are typically those suitable for parenteral administration including isotonic solutions, which include buffers, antioxidants and the like, as well as emulsions that include delivery vehicles such as liposomes, micelles and nanoparticles.

The desired protocols and formulations are dependent on the judgment of the attending practitioner as well as the specific condition of the subject. Dosage levels will depend on the age, general health and severity of infection, if appropriate, of the subject.

The following examples are offered to illustrate but not to limit the invention.

Example 1

Isolation of Human B Cells Secreting Antibody to CMV gB

Peripheral blood mononuclear cells from 50 adults with confirmed titer against CMV were surveyed for human B cells producing anti-viral antibodies. Subjects with the desired antibodies against CMV gB protein were used for cloning of specific mAbs. The result of the survey was that ~10% of the subjects had a frequency of the desired cells greater than 1 in 50,000.

To accomplish the survey and recovery of rare favorable cells, we used the previously described CellSpot™ technology (U.S. Pat. No. 7,413,868, incorporated herein by reference). The CellSpot™ assay method effectively shrinks an ELISA equivalent assay down to a virtual well of nearly single cell dimensions by capturing secreted IgG from a single cell as a footprint in the vicinity of the cell, so that millions of cells can be readily analyzed. Further, by use of microscopic multiplexing reagents (combinatorially colored fluorescent latex microspheres, cf U.S. Pat. No. 6,642,062, incorporated herein by reference), each clone's secreted antibody footprint can be characterized in detail for specificity and/or affinity using multiple biochemical probes. The fidelity of the quantitative assay is sufficient to enable rescue of extremely rare favorable cells from the survey population, with the cloned expression cell showing a phenotype consistent with the original identifying assay.

The screening criteria were binding to purified gB protein as well as to viral lysate. gB protein was purified from 293 cells infected with AD169 strain of CMV. Affinity rank ordering of clones is accomplished by diluting the antigen on the bead with serum albumin. This reduces the chances for multi-dentate binding to the secreted IgG footprint (an "avidity" effect), thus selecting for higher intrinsic affinity.

Non-B cells were depleted from PBMCs in plasma of human donors using standard magnetic separation methods. Cells were resuspended in IMDM/20% HI-FCS at 1e6/ml; and immortalized with EBV (direct pelleted from the supernatant of infected B95-8 cells). EBV was added at 1:100 dilution, and the cells incubated 2 hr at 37° C. Excess EBV was washed away, and cells either:

(1) cultured at 2e6/ml in IMDM, 20% HI-FCS, 20% Giant cell tumor conditioned medium, 2 µg/ml CpG (ODN2006), and 10 ng/ml IL-10 for surveying only, or
(2) further selected for surface IgG using magnetic positive selection.

Cells were cultured at 200-300 cells/well on irradiated human lung cells (MRC-5, 5,000 cells/well) in IMDM, 20% HI-FCS, 20% Giant cell tumor conditioned medium, 2 µg/ml CpG (ODN2006), and 10 ng/ml IL-10. Medium was supplemented every 2-3 days. One half of the contents of the wells were assayed in CellSpot™ at day 6. The remaining cells in the small number of wells positive by the survey assay were then diluted to 10, 5, 1, and 0.5 cells/well with the same feeder cells and culture conditions. After 4-5 days these limiting dilution plates were again assayed by ELISA or CellSpot™.

CellSpot™ nano-particles were conjugated with viral lysate or purified gB protein to screen for the desired antibodies. Lysate created from cells infected with the CMV AD169 virus was purchased from Virusys (cat #CV046). (The lysate is produced in Normal Human Dermal Fibroblast (NHDF) cell line.) Recombinant CMV gB antigen was produced as His-tagged fusion protein in 293 cells and purified using a nickel chelation column. Purified gB protein was used for ELISA and CellSpot. The preparations of AD169 lysate and gB purified protein were conjugated to nano-particles, respectively, as previously described, cf Harriman et al (supra) and Collarini et al (supra).

Contents of positive wells at limiting dilution were then processed using Reverse Transcriptase-PCR to recover the encoding mRNA for the antibody heavy and light chains. Total time from thawing PBMCs to recovery of the encoding mRNA sequence via RT-PCR was 10-12 days.

Example 2

Cloning of Human Antibodies to CMV gB

Amplification of rearranged Ig Heavy and Ig Light genes from positive ELISA wells was accomplished using seminested polymerase chain reaction (PCR). For amplification of a previously unknown V-gene rearrangements, a collection of family-specific V-gene primers was constructed, which recognize nearly all V-gene segments in the human Ig Locus. The 5' primers were used together with primer mixes specific for the Cγ, Cκ and Cλ gene segments. The clonality of the limiting dilution CMV-gB specific B cells was unequivocally determined by sequence comparison of V-gene amplificates from distinct progeny cells, and the amplified full length V-gene rearrangements were cloned into IgG expression vectors.

In detail, total mRNA from the isolated human B cells was extracted using a commercially available RNA purification kit (RNeasy™; Qiagen (Germany)). Reverse transcription-PCR was done by using total RNA preparations and oligo-nucleotides as primers. Three PCR reactions were run for each sample: one for light chain kappa (κ) one for light chain lambda (λ), and one for gamma heavy chain (γ). The QIAGEN® OneStep RT-PCR kit was used for amplification, (Qiagen Catalog No. 210212). In the coupled RT-PCR reactions, cDNA is synthesized with unique blend of RT enzymes (Omniscript™ and Sensiscript™) using antisense sequence specific primer corresponded to C-κ, C-λ or to a consensus of the CH1 regions of Cγ genes, RT is preformed at 50° C. for 1 hour followed by PCR amplification of the cDNA by HotStarTaq DNA Polymerase for high specificity and sensitivity. Each PCR reaction used a mixture of 5' sense primers. Primer sequences were based on leader sequences of VH, VK and VL. PCR reactions were run at 95° C. for 15 minutes, initial hot start followed by 20 cycles of 95° C. for 30 seconds (denaturation), 60° C. for 45 seconds (annealing) and 72° C. for 1 minute (elongation).

Nested PCR for Detection and Cloning of the Variable Ig Fragments into Expression Vectors.

In the second round, an aliquot of 5 µl of the first amplification reaction was applied. The primers used carry the 5'BglII and 3' XbaI restriction sites. Thirty PCR cycles were performed. Identical conditions were used for the first and second rounds of amplification. Five microliters of each reaction were loaded and separated on a 1% agarose gel and then stained with ethidium bromide. The V-C PCR product is predicted to amplify rearranged fragments of VH and VL, 500 and 450 by respectively. PCR bands with a molecular size of approximately 500 by indicated a positive result. PCR products were purified (Qiagen gel purification kit catalog number 28704) and the extracted PCR products were directly sequenced using specific constant region primers. The sequences of the cloned fragments were confirmed by sequencing plasmids prepared for recombinant production.

The PCR fragments described above were digested and cloned into individual expression vectors carrying the constant region of human gamma 1, or of human kappa or lambda, for in vitro antibody production in mammalian cells. The expression vectors coding for heavy and light chains were co-transfected into the 293 (human kidney) cell line (Invitrogen). The expression plasmids were introduced with the use of a cationic lipid-based transfection reagent (293fectin™; Invitrogen). For each transfection reaction, 20 µg of purified plasmids and 40 µL of the 293fectin™ were mixed with 1 mL of Opti-MEM® (Invitrogen) and incubated for 5 min at room temperature before being combined and allowed to form complexes for 20 min at room temperature. The DNA-293fectin complexes were added to 3×10⁶ cells seeded in 90 mm petri plates and incubated at 37° C., 8% CO2. In the final procedure, the supernatant was harvested 72 hrs post-transfection by centrifugation (3,000 g, 15 min at 4° C.), to recover the secreted antibodies.

From ~2 million lymphocytes, 45 clones were isolated which bound the AD169 lysate. Of these, the majority also bound the recombinant gB protein.

Two of the mAbs that bound both AD169 and gB (4A2 and 19B10) had neutralizing capability. One of these (4A2) binds the AD-2 peptide, which is a conserved site on the gB protein. An additional mAb (5C5) binds AD-2 but does not neutralize the virus.

The amino acid sequences of the heavy and light chains of 4A2 and 19B10, including variable region, the D and J joining regions, the framework (FR) and complementarity determining (CDR) regions, are shown below. The secretion signal sequence on the heavy chain is italicized, and CDRs 1-3 are underlined.

```
4A2 HC, VH3-30 nucleic acid (SEQ ID NO: 1) and amino
acid (SEQ ID NO: 2)
atggaattgggctgagctgggttttcgtcgttgctcttttaagaggtgtccagtgtcaa
 M   E   L   G   L   S   W   V   F   V   V   A   L   L   R   G   V   Q   C   Q
gtgttgttggaggagtctgggggaggcgtggtccagcctgggaggtctctgagactctcc
 V   L   L   E   E   S   G   G   G   V   V   Q   P   G   R   S   L   R   L   S
tgtgcaggctctggattcaccttcaataggcatggaattcactgggtccgccaggctcca
 C   A   G   S   G   F   T   F   N   R   H   G   I   H   W   V   R   Q   A   P
ggcaagggctggagtgggtgactgttatatcatctgatggagcaaatcaacagtatgca
 G   K   G   L   E   W   V   T   V   I   S   S   D   G   A   N   Q   Q   Y   A
gagtccgtgaagggccgattcatcatctccagagacaattccaagaacacggtatatcta
 E   S   V   K   G   R   F   I   I   S   R   D   N   S   K   N   T   V   Y   L
gaaatgaatagcctgaggaatgacgacacgggtgtgtatttctgcgcgagagacggtcgt
 E   M   N   S   L   R   N   D   D   T   G   V   Y   F   C   A   R   D   G   R
tgtgaaggcgagaggtgctactccggtgtcacggacttctggggcagggaacactggtc
 C   E   G   E   R   C   Y   S   G   V   T   D   F   W   G   Q   G   T   L   V 4A2 LC L6, IgKV3-11 nucleic acid (SEQ ID NO: 3) and amino
acid (SEQ ID NO: 4)
atggaagccccagcgcagcttctcttcctcctgctactctggctcccagataccaccgga
 M   E   A   P   A   Q   L   L   F   L   L   L   L   W   L   P   D   T   T   G
gaaattgtattgacacagtctccagccaccctgtctttgtctccaggggagagagccacc
 E   I   V   L   T   Q   S   P   A   T   L   S   L   S   P   G   E   R   A   T
ctctcctgcagggccagtcagaatattggcggctacttggcctggttccaacaaaaagct
 L   S   C   R   A   S   Q   N   I   G   G   Y   L   A   W   F   Q   Q   K   A
ggccaggctcccaggctcctcatctatgatgcatccatcagggccactggcatcccagcc
 G   Q   A   P   R   L   L   I   Y   D   A   S   I   R   A   T   G   I   P   A
aggttcagtggcagtgggtctgggacagacttcactctcaccatcagcagcctagagcct
 R   F   S   G   S   G   S   G   T   D   F   T   L   T   I   S   S   L   E   P
```

```
                         -continued
gaagattttgcagtttattactgtcagcagcgtaacagttggcctccactcactttcggc
  E   D   F   A   V   Y   Y   C   Q Q R N S W P P L T   F   G 19B10 HC VH4-31, D2, J6 nucleic acid (SEQ ID NO: 5) and amino
acid (SEQ ID NO: 6)
atgaaacatctgtggttcttcctcctgctggtggcagctcccagatgggtcctgtcccag
  M   K   H   L   W   F   F   L   L   L   V   A   A   P   R   W   V   L   S   Q
gtgcagctgcagcagtcgggcccaggactggtgaagccttcacagaccctgtccctcacc
  V   Q   L   Q   Q   S   G   P   G   L   V   K   P   S   Q   T   L   S   L   T
tgcactgtctctggtggctccatcagtagcggtgattttgctggaattggatccgccag
  C   T   V   S   G   G S I S S G D F C W N   W   I   R   Q
ccccagggaagggcctggagtggattgggtacatctgttacaccggggacacctactac
  P   P   G   K   G   L   E   W   I   G   Y I C Y T G D   T   Y   Y
aacccgcccttaacagtcgagttaccatatcagtcgacaggtccaggaaccaaatctcc
  N   P   P   L   N   S   R   V   T   I   S   V   D   R   S   R   N   Q   I   S
ctgaggctgagttctgtgactgccgcagacacggccgtgtattattgtgccagagaggat
  L   R   L   S   S   V   T   A   A   D   T   A   V   Y   Y   C   A R E D
aggagacaactacactctcgcccctacttctactacggttttggacgtctggggccgaggg
  R R Q L H S R P Y F Y Y G L D V   W   G   R   G
accaaggtcaccgtctcctcagcttccaccaagggcccatcggtcttccccctggtaccc
  T   K   V   T   V   S   S   A   S   T   K   G   P   S   V   F   P   L   V   P
tctagc
  S   S 19B10 LC, A3, IgKV2 nucleic acid (SEQ ID NO: 7) and amino
acid (SEQ ID NO: 8)
atgaggctccctgctcagcttctggggctgctaatgctctgggtctctggatccagtggg
  M   R   L   P   A   Q   L   L   G   L   L   M   L   W   V   S   G   S   S   G
gagattgtgatgactcagtctccgctctccctgcccgtcacccctggagagacggcctcc
  E   I   V   M   T   Q   S   P   L   S   L   P   V   T   P   G   E   T   A   S
atctcctgcaggtctagtcagagcctcctgcatagtaatggacacaactatttggattgg
  I   S   C   R   S   S   Q S L L H S N G H N Y L D   W
tatctgcagaagccagggcagtctccacacctcctgatctatttgggttctattcgggcc
  Y   L   Q   K   P   G   Q   S   P   H   L   L   I   Y   L G S I R A
tccggggtccctgacaggttcagtggcagtggaacaggcacagattttacactgaaaatc
  S   G   V   P   D   R   F   S   G   S   G   T   G   T   D   F   T   L   K   I
agcagagtggaggctgaggatgttggggtttattactgcatgcaagctctacaaactcct
  S   R   V   E   A   E   D   V   G   V   Y   Y   C   M Q A L Q T P
aacactttggccaggggaccaagctggagatcagacgaactgtggctgcaccatctgtc
  N T   F   G   Q   G   T   K   L   E   I   R   R   T   V   A   A   P   S   V
```

High affinity antibodies were generated by preparing CellSpot probes coated with full length gB protein or with the Ad-2 peptide at either high or low density on the fluorescent bead. Without being constrained by theory, since low density reduces the multi-dentate avidity effect, the search is biased in favor oa antibodies with high intrinsic affinity. Multiple high affinity antibodies were isolated and sequenced. The sequences of other monoclonal antibodies that are reactive to CMV were determined, and are shown as SEQ ID NOs:9-36, and 38-66. The nucleotide sequence of the human IgG1 heavy chain constant region is shown in SEQ ID NO:37.

In antibodies of the invention, the heavy chain can have a CDR1 of GFTFNRHG (SEQ ID NO:67) or GSISSEDFC (SEQ ID NO:68); and/or a CDR2 region of SSDGANQ (SEQ ID NO:69) or ICYTGD (SEQ ID NO:70); and/or a CDR3 region of ARDGRCEGERCYSGVTDF (SEQ ID NO:71) or AREDRRQLHSRPYFYYGLDV (SEQ ID NO:72). In other embodiments, the light chain has a CDR1 region of QNIGGY (SEQ ID NO:73) or QSLLHSNGHNY (SEQ ID NO:74); and/or a CDR2 region of DAS (SEQ ID NO:75) or LG (SEQ ID NO:76); and/or a CDR3 region of QQRNSWPPLT (SEQ ID NO:77) or QALQTPNT (SEQ ID NO:78).

Example 3

Affinity Determination

The affinity of the invention antibodies was determined by FortéBio® (Menlo Park, Calif.) biosensor analysis. In this method, the carboxylic acid groups on Amine Reactive Biosensors were activated with EDC/NHS. Antibody, diluted in MES buffer at pH 5, was attached to the activated surface of the probe and the remaining active carboxylated groups were blocked with ethanolamine. The gB protein was incubated with the Ab-coated probe and rates of association to and dissociation from the Ab-coated probe were determined by the FortéBio® instrument.

In one experiment, 4A2 was found to have an affinity of 168 pM and 19B10 an affinity of 697 pM, as shown as corresponding $IC_{50}$ in µg/ml in Table 1. These affinity constants are substantially better than for published monoclonal antibodies to gB.

TABLE 1

Comparison of neutralizing potency of mAbs.

| mAb (target) | IC50 (µg/mL) | citation | source |
|---|---|---|---|
| 4A2 (gB) | 0.02 | — | human |
| 19B10 (gB) | 0.04 | — | human |
| CH177 (gB) | 0.23 | Nozawa, N, et al. (2009) supra | murine |
| G3D (gB) | 0.50 | Nakajima, N., et al. (2009) supra | human |
| 10C6 (gB) | 0.30 | Lanzavecchia, A., et al. (2009) supra | human |

The binding affinity of mAbs 310, 313, 345, and 4A2 to the AD-2 epitope of gB was determined. The gB binding kinetics are shown in Table 2. The mAbs 310, 313, and 338 have about 10× higher potency than mAb 4A2. The mAbs 323, 316, and 338 also have higher potency than mAb 4A2 (data not shown). The binding affinities of the remaining mAbs are also tested and also better than for published monoclonal antibodies to gB.

TABLE 2

| mAb | ka (× 10⁴) (1/Ms) | kd (× 10⁻⁵) (1/s) | KD nM |
|---|---|---|---|
| 4A2 | 58 | 9.5 | 16 |
| 310 | 1.6 | 1.2 | 0.8 |
| 313 | 1.7 | 1.2 | 0.7 |
| 345 | 1.4 | 3.3 | 2.3 | gB binding kinetics

Example 4

ELISA Binding Assay and Epitope Mapping

The mAbs 4A2 and 19B 10 were assessed for binding to purified gB protein and to a conserved peptide designated AD-2: NETIYNTTLKYGDV (SEQ ID NO:79). 4A2 binds well to both full length protein and peptide AD-2, whereas 19B10 only binds the protein.

Example 5

Virus Neutralization Assay

The mAbs 4A2 and 19B10 neutralized the AD169 strain of CMV in MRC5 primary fibroblasts. Serial dilutions of the antibodies were mixed with an equal volume of AD 169 (10⁸/ml stock diluted to give 2000 infected cells per well) and incubated for 1 h at room temperature before addition to target cell monolayers in 96-well microplates. After 24 h, cells were fixed, permeabilized, and stained with monoclonal antibody against IE1 (Intermediate Early protein 1, also known as UL123, a marker of replicating virus) conjugated to HRP. The infected cells were detected following deposition of HRP substrate. The number of infected cells was plotted against the concentration of the antibody.

Virus neutralization was also assessed using the VR1814 strain (Revello, et al., *J. Gen. Virol.* (2001) 82:1429-1438). The mAbs 4A2, 310, 313, 338, and 345 neutralized the VR1814 strain in both human umbilical vein endothelial cells (HUVEC) and human foreskin fibroblast (HFF) cells. Table 3 and Table 4 show the IC50 and IC90 values, respectively, for each of mAbs 4A2, 310, 313, 338, and 345.

TABLE 3

Virus strain VR1814: IC50 (µg/ml)

|  | HUVEC | HFF |
|---|---|---|
| 4A2 | ~1.0 | 1.32 |
| 310 | 0.30 | 0.53 |
| 313 | 0.37 | 0.37 |
| 338 | 0.24 | 0.63 |
| 345 | 0.13 | 0.18 |

TABLE 4

Virus strain VR1814: IC90 (µg/ml)

|  | HUVEC | HFF |
|---|---|---|
| 4A2 | 6.81 | 7.09 |
| 310 | 3.59 | 5.28 |
| 313 | 4.30 | 1.51 |
| 338 | 2.62 | >10 |
| 345 | 0.97 | 0.89 |

Figure 2:
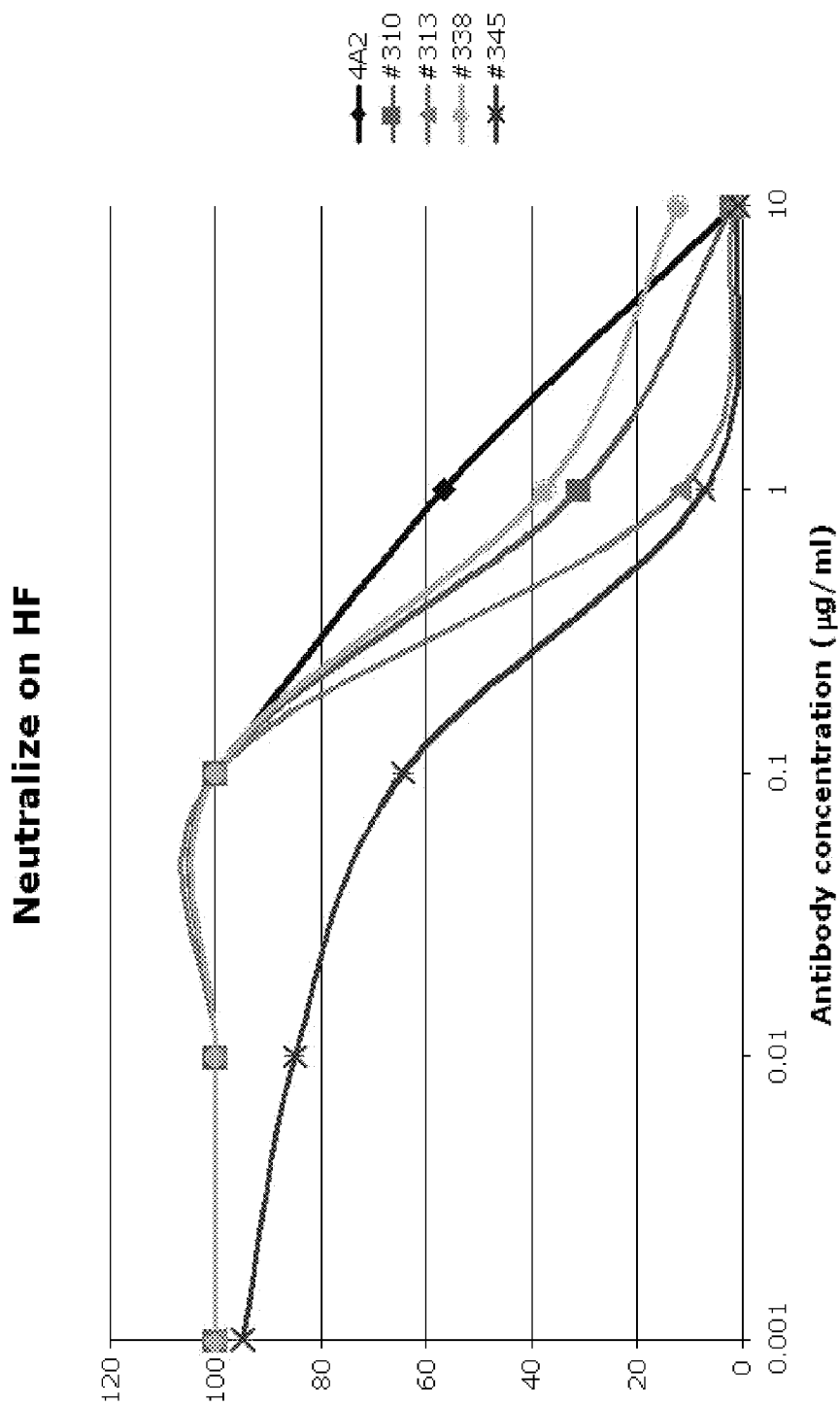
FIG. 2 shows the neutralization of VR1814 by mAbs 4A2, 310, 313, 338, and 345 in HFF cells.

FIGS. 1 and 2 show the neutralization of HUVEC and HFF cells, respectively, by each of the mAbs 4A2, 310, 313, 338, and 345. The results were tested in duplicate. MAB345 was deposited under the terms of the Budapest Treaty at the American Type Culture Collection (ATCC), 10801 University Boulevard, Manassas, Va., 20110, USA, on Nov. 4, 2014 and given ATCC deposit designation PTA-121705.

Other mAbs are also tested, which neutralize the AD169 and VR1814 strains.

SEQUENCE LISTING

```
4A2 HC, VH3-30 nucleic acid (SEQ ID NO: 1) and amino acid
(SEQ ID NO: 2)
atggaattggggctgagctgggttttcgtcgttgctcttttaagaggtgtccagtgtcaa
 M  E  L  G  L  S  W  V  F  V  V  A  L  L  R  G  V  Q  C  Q
gtgttgttggaggagtctggggggaggcgtggtccagcctggggaggtctctgagactctcc
 V  L  L  E  E  S  G  G  G  V  V  Q  P  G  R  S  L  R  L  S
tgtgcaggctctggattcaccttcaataggcatgaattcactgggtccgccaggctcca
 C  A  G  S  G  F  T  F  N  R  H  G  I  H  W  V  R  Q  A  P
ggcaagggggctggagtgggtgactgttatatcatctgatggagcaaatcaacagtatgca
 G  K  G  L  E  W  V  T  V  I  S  S  D  G  A  N  Q  Q  Y  A
gagtccgtgaagggccgattcatcatctccagagacaattccaagaacacggtatatcta
 E  S  V  K  G  R  F  I  I  S  R  D  N  S  K  N  T  V  Y  L
gaaatgaatagcctgaggaatgacgacacgggtgtgtatttctgcgcgagagacggtcgt
 E  M  N  S  L  R  N  D  D  T  G  V  Y  F  C  A  R  D  G  R
tgtgaaggcgagaggtgctactccggtgtcacggacttctggggccagggaacactggtc
 C  E  G  E  R  C  Y  S  G  V  T  D  F  W  G  Q  G  T  L  V 4A2 LC L6, IgKV3-11 nucleic acid (SEQ ID NO: 3) and amino
acid (SEQ ID NO: 4)
atggaagcccccagcgcagcttctcttcctcctgctactctggctcccagataccaccgga
 M  E  A  P  A  Q  L  L  F  L  L  L  L  W  L  P  D  T  T  G
gaaattgtattgacacagtctccagccaccctgtctttgtctccaggggagagagccacc
 E  I  V  L  T  Q  S  P  A  T  L  S  L  S  P  G  E  R  A  T
ctctcctgcagggccagtcagaatattggcggctacttggcctggttccaacaaaaagct
 L  S  C  R  A  S  Q  N  I  G  G  Y  L  A  W  F  Q  Q  K  A
ggccaggctcccaggctcctcatctatgatgcatccatcagggccactggcatcccagcc
 G  Q  A  P  R  L  L  I  Y  D  A  S  I  R  A  T  G  I  P  A
```

```
aggttcagtggcagtgggtctgggacagacttcactctcaccatcagcagcctagagcct
 R   F   S   G   S   G   S   G   T   D   F   T   L   T   I   S   S   L   E   P
gaagattttgcagtttattactgtcagcagcgtaacagttggcctccactcactttcggc
 E   D   F   A   V   Y   Y   C   Q   Q   R   N   S   W   P   P   L   T   F   G
```

19B10 HC VH4-31, D2, J6 nucleic acid (SEQ ID NO: 5) and
amino acid (SEQ ID NO: 6)
```
atgaaacatctgtggttcttcctcctgctggtggcagctcccagatgggtcctgtcccag
 M   K   H   L   W   F   F   L   L   L   V   A   A   P   R   W   V   L   S   Q
gtgcagctgcagcagtcgggcccaggactggtgaagccttcacagaccctgtccctcacc
 V   Q   L   Q   Q   S   G   P   G   L   V   K   P   S   Q   T   L   S   L   T
tgcactgtctctggtggctccatcagtagcggtgattttgctggaattggatccgccag
 C   T   V   S   G   S   I   S   S   G   D   F   C   W   N   W   I   R   Q
cccccagggaagggcctggagtggattgggtacatctgttacaccggggacacctactac
 P   P   G   K   G   L   E   W   I   G   Y   I   C   Y   T   G   D   T   Y   Y
aacccgcccctaacagtcgagttaccatatcagtcgacaggtccaggaaccaaatctcc
 N   P   P   L   N   S   R   V   T   I   S   V   D   R   S   R   N   Q   I   S
ctgaggctgagttctgtgactgccgcagacacggccgtgtattattgtgccagagaggat
 L   R   L   S   S   V   T   A   A   D   T   A   V   Y   Y   C   A   R   E   D
aggagacaactacactctcgcccctacttctactacggttcgacgtctggggccgaggg
 R   R   Q   L   H   S   R   P   Y   F   Y   Y   G   L   D   V   W   G   R   G
accaaggtcaccgtctcctcagcttccaccaagggcccatcggtcttccccctggtaccc
 T   K   V   T   V   S   S   A   S   T   K   G   P   S   V   F   P   L   V   P
tctagc
 S   S
```

19B10 LC, A3, IgKV2 nucleic acid (SEQ ID NO: 7) and amino
acid (SEQ ID NO: 8)
```
atgaggctccctgctcagcttctggggctgctaatgctctgggtctctggatccagtggg
 M   R   L   P   A   Q   L   L   G   L   L   M   L   W   V   S   G   S   S   G
gagattgtgatgactcagtctccgctctccctgcccgtcacccctggagagacggcctcc
 E   I   V   M   T   Q   S   P   L   S   L   P   V   T   P   G   E   T   A   S
atctcctgcaggtctagtcagagcctcctgcatagtaatggacacaactatttggattgg
 I   S   C   R   S   S   Q   S   L   L   H   S   N   G   H   N   Y   L   D   W
tatctgcagaagccagggcagtctccacacctcctgatctatttgggttctattcgggcc
 Y   L   Q   K   P   G   Q   S   P   H   L   L   I   Y   L   G   S   I   R   A
tccggggtccctgacaggttcagtggcagtggaacaggcacagatttacactgaaaatc
 S   G   V   P   D   R   F   S   G   S   G   T   G   T   D   F   T   L   K   I
agcagagtggaggctgaggatgttggggtttattactgcatgcaagctctacaaactcct
 S   R   V   E   A   E   D   V   G   V   Y   Y   C   M   Q   A   L   Q   T   P
aacacttttggccaggggaccaagctggagatcagacgaactgtggctgcaccatctgtc
 N   T   F   G   Q   G   T   K   L   E   I   R   R   T   V   A   A   P   S   V
```

Human IgG1 HC amino acid sequence of constant region
(SEQ ID NO: 9)
ASTKGPSVFPLVPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK MAB297 HC variable domain amino acid sequence (SEQ ID NO: 10)
QVQLVQSGGGVVQPGRSLRLSCSASGFTFSNYNMHWVRQAPGKGPEWVAVISKDGNEKHY
AESAKGRFTISRDNSKNTLYMEMHSLTPEDTAMYYCTRDGRTDGTGYSGILDIWGQGTKV
IVS MAB309 and 318 HC variable domain amino acid sequence
(SEQ ID NO: 11)
QVQLVQSGGGVVQPGTSLRLSCAASGFMFNTYNMHWVRQAPGKGLEWVAVISNDGTYKHF
ADSLKGRFSISRDDSKNTLYLHMNSLRPDDTAIYYCARDGRSVGGFSGILDPWGQGTLVT
VSS MAB310 HC variable domain amino acid sequence (SEQ ID NO: 12)
QVQLVQSGGGVVQPGTSLRLSCAASGFMFNTYNMHWVRQAPGKGLEWVAVISNDGTYKYS
ADSLKGRFSISRDNSKNTLYLHMNSLRPDDTAVYYCARDGRSVGGFSGILDPWGQGTLVT
VSS MAB313 HC variable domain amino acid sequence (SEQ ID NO: 13)
QVQLVQSGGGVIQPGRSLTLSCAASGFTFSAYSLHWVRQAPGKGLQWVAVISFDGNFKHF
ADSLRGRFTISRDNSKNRFYLQMNGLRGEDTAVYYCARDGRAVDGFSGILDFWGQGTLVS
VSS MAB314 HC variable domain amino acid sequence (SEQ ID NO: 14)
QVQLQESGGGLVQPGGSLKLSCAVSGFSFGGSAMHWVRQASGKGLEWIGHIRSGANNFET
AYAPSLDGRFTISRDDSKNTAYLHMNSLKTDDTAMYFCTTGLIASGDANFDYWGQGTQVT
VSS

SEQUENCE LISTING

MAB316 HC variable domain amino acid sequence (SEQ ID NO: 15)
QVQLVQSGGGVVQPGRSLTLSCAASGFTFSGFSLHWVRQAPGKGLQWVAVISFDGNHKHF
ADSLKGRFTISRDNSKNTLYLQINDLRGEDTAVYYCARDGRAVDGFSGILDFWGQGTLVS
VSS MAB319 HC variable domain amino acid sequence (SEQ ID NO: 16)
QVQLVESGGGVVQPGRSLRLSCSASGFTFSDYNLHWVRQAPGKGLEWVAVISIDGSDKHH
ADSVKGRFTVSRDNSKNTVSLQMDSLRPEDTAVYYCARDGRSVGGYSGILDPWGQGTLVT
VSS MAB321 HC variable domain amino acid sequence (SEQ ID NO: 17)
EVQLVESGAEVKKPGESLKISCQGSGYRFTNYWIAWVRQMPGKGLEWMGIIYPGDSDTRY
HPSFQGQVTISSDKSLNTAYLQWSSLKPSDTAVYYCARHHCLSTNCQTAVAGYNDYWGQG
NPGRRLLS MAB322 HC variable domain amino acid sequence (SEQ ID NO: 18)
QVQLVQSGGGVVQPGRSLRLSCSASGFTFTNYNMHWVRQAPGKGLEWVAVTSKDGNEKHF
ADSVKGRFTISRDNSKNTLYLEMNTLTAEDTAIYYCTRDGRTDGTGYSGILDIWGQGTKV
TVSS MAB323 HC variable domain amino acid sequence (SEQ ID NO: 19)
QVQLVQSGGGVVQPGRSLRLSCAASGFTFSNFAMHWVRQAPGKGLEWVAVISNAGRETHY
ADSVKGRFTVSRDNSKNMLSLQMNSLRGEDTAVYYCARDGRTDGSGYSGVLDIWAQGTLV
TVSS MAB338 HC variable domain amino acid sequence (SEQ ID NO: 20)
QVQLVESGGGVVQPGRSLRLSCSGSGFTFSDYNLHWVRQAPGKGLEWVAVISIDGTNKHH
ADSVKGRFTISRDNSKNTVNLEMSRLKAEDTAVYYCVRDGRSIGGYSGIFDPWGQGTLVT
VSS MAB343 HC variable domain amino acid sequence (SEQ ID NO: 21)
QVQLQESGGGVVQPGRSLRLSCAASGFTFNTYNMHWVRQAPGKGLEWVAVISNDGTYKYS
ADSVKGRFSISRGNSKNTLYLQMNSLRPDDTAVYYCARDGRSVGGFSGILDPWGQGTLAT
VSS MAB345 HC variable domain amino acid sequence (SEQ ID NO: 22)
QVQLVESGGGVVQPGRSLRLSCAASGFTFSDYNMHWVRQAPGKGLEWVAVISIDGTYKYS
ADSVAGRFSLSRDNSKNTLYLQMNSLRPDDTAIYYCARDGRSVGGFSGILDPWGQGTLVT
VSS Human LC amino acid sequence of constant kappa region
(SEQ ID NO: 23)
TVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC MAB297 and MAB322 LC variable domain amino acid sequence
(SEQ ID NO: 24)
EIVMTQSPATLSLSPGERATLSCRASQSVGGYLAWYQQKPDQAPRLLIYDVSNRAAGIPA
RFSGSGSGTDFTLTISSLEPEDFAVYYCQQRNTWPPLTFGGGTKVEIKR MAB309 LC variable domain amino acid sequence (SEQ ID NO: 25)
EIVLTQSPATLSLSPGDRATLSCRASQTVGRYLAWYQQKPGQAPRLLIYDASDRATGISA
RFSGSGSGTDFTLTISSLEPEDFAVYYCQQRSSWPPLTFGGGTKVEIKR MAB310 LC variable domain amino acid sequence (SEQ ID NO: 26)
EIVLTQSPATLSLSPGDRATLSCRASQTVGRYLAWYQQKPGQAPRLLIYDASDRATGISA
RFSGSGSGTDFTLTISSLEPEDFAVYYCQQRSNWPPLTFGGGTKVEIKR MAB313 LC variable domain amino acid sequence (SEQ ID NO: 27)
EIVMTQSPATLSLSPGERATLSCRASQSVGRYLTWFQQKPGQAPRLLIYDASERATGIPA
RFSGSGSGTDFTLTISSLEPEDFAVYYCQQRANWPPLTFGGGTKVEIK MAB314 LC variable domain amino acid sequence (SEQ ID NO: 28)
EIVMTQSPGTLSLFPGERATLSCRASQTVRNGYLAWYQQKPGQAPRLLIYGASIRATGIP
DRFSGSGSETDFTLSITRVEPEDFAVYYCQQYGRLSSTFGQGTKLDLK MAB316 LC variable domain amino acid sequence (SEQ ID NO: 29)
EIVMTQSPATLSLSPGERATLSCRASQSVGRYLTWFQQKPGQAPRLLIYDASERATGVPA
RFSGSGSGTDFTLTISSLEPEDFAVYYCQQRSNWPPLTFGGGTKVEIK MAB318 LC variable domain amino acid sequence (SEQ ID NO: 30)
EVVLTQSPATLSLSPGDRATLSCRASQTVGRYLAWYQQKPGQAPRLLIYDASDRATGISA
RFSGSGSGTDFTLTIGSLEPEDFAVYYCQQRSSWPPLTFGGGTKVEIK MAB319 LC variable domain amino acid sequence (SEQ ID NO: 31)
EIVLTQSPATLSLSPGERATLSCRASQSVGSYLAWYQQKPGQAPRLLIYDASERATGIPA
RFSGSGSGTDFTLTISSLEPEDVAVYYCQQRNNWPPLTFGGGTKVEIK MAB321 LC variable domain amino acid sequence (SEQ ID NO: 32)
EIVMTQSPDSLAVSLGERATINCKSSQSILFSSKNQNHLAWYQQKPGQPPKLLIYWASTR
ESGVPDRFSGSGSGTDFTLTISSLQAEDVAVYYCQQYYNIPHTFGGGTKVEIK MAB323 LC variable domain amino acid sequence (SEQ ID NO: 33)
EIVLTQSPATLSLSPGERATLSCRASQSVNRYLAWFQHRPGQPPRLLIYDASKRATGIPA
RFSGSGSGTDFTLTISSLEPEDFAVYYCQQRSNWPLTFGGGTKVEIK MAB338 LC variable domain amino acid sequence (SEQ ID NO: 34)
EIVLTQSPATLSLSPGERATLSCRASQSVDRYLAWYQQKPGQAPRLLIYDASQRATGIPA
RFSGSGSGTDFTLAISSLEPEDVAVYYCQQRSNWPPLTFGGGTKIEIK MAB343 LC variable domain amino acid sequence (SEQ ID NO: 35)
EIVMTQSPATLSLSPGDRATLSCRASQSVGSYLAWYQQKPGQAPRLLIYDASDRATGIPA
RFSGSGSGTDFTLTISSLEPEDFAVYYCQQRSNWPPLTFGGGTKVEIK MAB345 LC variable domain amino acid sequence (SEQ ID NO: 36)
EIVMTQSPATLSLSPGDRATLSCRASQSVGSYLAWYQQKPGQAPRLLMYDSSVRATGIPA
RFSGSGSGTDFTLTISSLEPEDFAVYYCQQRNNWPPLTFGGGTKVEIK Human IgG1 HC nucleotide sequence of constant region
(introns are underlined) (SEQ ID NO: 37)
GCCTCCACCAAGGGCCCATCAGTCTTCCCCCTGGCACCCTCCTCCAAGAGCACCTCTGGG
GGCACAACGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGGTGAG
AGGCCAGCACAGGGAGGGAGGGTGTCTGCTGGAAGCCAGGCTCAGCGCTCCTGCCTGGAC
GCATCCCGGCTATGCAGTCCCAGTCCAGGGCAGCAAGGCAGGCCCCGTCTGCCTCTTCAC
CCGGAGGCCTCTGCCCGCCCCACTCATGCTCAGGGAGAGGGTCTTCTGGCTTTTTCCCCA
GGCTCTGGGCAGGCACAGGCTAGGTGCCCCTAACCCAGGCCCTGCACACAAAGGGGCAGG
TGCTGGGCTCAGACCTGCCAAGAGCCATATCCGGGAGGACCCTGCCCCTGACCTAAGCCC
ACCCCAAAGGCCAAACTCTCCACTCCCTCAGCTCGGACACCTTCTCTCCTCCCAGATTCC
AGTAACTCCCAATCTTCTCTCTGCAGAGCCCAAATCTTGTGACAAAACTCACACATGCCC
ACCGTGCCCAGGTAAGCCAGCCCAGGCCTCGCCCTCCAGCTCAAGGCGGGACAGGTGCCC
TAGAGTAGCCTGCATCCAGGGACAGGCCCCAGCCGGGTGCTGACACGTCCACCTCCATCT
CTTCCTCAGCACCTGAACTCCTGGGGGGACCGTCAGTCTTCCTCTTCCCCCCAAAACCCA
AGGACACCCTCATGATCTCCCGGACCCCTGAGGTCACATGCGTGGTGGTGGACGTGAGCC
ACGAAGACCCTGAGGTCAAGTTCAACTGGTACGTGGACGGCGTGGAGGTGCATAATGCCA
AGACAAAGCCGCGGGAGGAGCAGTACAACAGCACGTACCGTGTGGTCAGCGTCCTCACCG
TCCTGCACCAGGACTGGCTGAATGGCAAGGAGTACAAGTGCAAGGTCTCCAACAAAGCCC
TCCCAGCCCCCATCGAGAAAACCATCTCCAAAGCCAAAGGTGGGACCCGTGGGGTGCGAG
GGCCACATGGACAGAGGCCGGCTCGGCCCACCCTCTGCCCTGAGAGTGACCGCTGTACCA
ACCTCTGTCCCTACAGGGCAGCCCCGAGAACCACAGGTGTACACCCTGCCCCCATCCCGG
GAGGAGATGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCT
CCCGTGCTGGACTCCGACGGCTCCTTCTTCCTCTATAGCAAGCTCACCGTGGACAAGAGC
AGGTGGCAGCAGGGGAACGTCTTCTCATGCTCCGTGATGCATGAGGCTCTGCACAACCAC
TACACGCAGAAGAGCCTCTCCCTGTCCCCGGGTAAATGA MAB297 HC variable domain nucleotide sequence (SEQ ID NO: 38)
CAGGTGCAACTGGTGCAGTCTGGGGGAGGCGTGGTCCAGCCTGGGAGGTCCCTGAGACTC
TCCTGTTCAGCCTCTGGATTCACCTTCAGCAACTATAATATGCACTGGGTCCGCCAGGCT
CCAGGCAAGGGGCCGGAGTGGGTGGCAGTTATATCAAAAGATGGAAACGAAAAACACTAT
GCAGAGTCTGCGAAGGGCCGATTCACCATCTCCAGAGACAATTCCAAGAACACGCTGTAT
ATGGAAATGCACAGCCTGACACCTGAGGACACGGCTATGTATTACTGTACGAGAGATGGG
CGAACCGATGGTACTGGGTACTCCGGTATTCTTGATATCTGGGGCCAAGGGACAAAGGTC
ATCGTCTCT MAB309 and 318 HC variable domain nucleotide sequence
(SEQ ID NO: 39)
CAGGTGCAGCTGGTGCAGTCTGGGGGAGGCGTGGTCCAGCCTGGGACGTCCCTGAGACTC
TCCTGTGCAGCCTCTGGATTCATGTTCAATACCTATAATATGCACTGGGTCCGCCAGGCT
CCAGGCAAGGGGCTGGAGTGGGTGGCAGTTATATCAAATGATGGAACCTATAAGCATTTC
GCTGACTCCCTGAAGGGCCGATTCAGCATCTCCAGAGACGATTCCAAGAACACGCTGTAT
CTGCACATGAACAGCCTGAGACCTGACGACACGGCTATATATTACTGTGCGAGAGATGGC
CGTAGTGTTGGCGGGTTTAGTGGGATCCTCGACCCCTGGGGCCAGGGAACCCTGGTCACC
GTCTCCTCAG MAB310 HC variable domain nucleotide sequence (SEQ ID NO: 40)
CAGGTGCAGCTGGTGCAGTCTGGGGGAGGCGTGGTCCAGCCTGGGACGTCCCTGAGACTC
TCCTGTGCAGCCTCTGGATTCATGTTCAATACCTACAATATGCACTGGGTCCGCCAGGCT

```
CCAGGCAAGGGGCTGGAGTGGGTGGCAGTTATATCAAATGATGGAACCTATAAGTACTCC
GCTGACTCCCTGAAGGGCCGATTCAGCATCTCCAGAGACAATTCCAAGAACACGTTGTAT
CTGCACATGAACAGCCTGAGACCTGACGACACGGCTGTATATTACTGTGCGAGAGATGGC
CGTAGTGTTGGCGGGTTTAGTGGGATCCTCGACCCCTGGGGCCAGGGAACCCTGGTCACC
GTCTCCTCAG

MAB313 HC variable domain nucleotide sequence (SEQ ID NO: 41)
CAGGTGCAGCTGGTGCAGTCTGGGGGAGGCGTGATCCAGCCTGGGAGGTCCCTGACACTC
TCCTGTGCAGCCTCTGGATTCACCTTCAGTGCCTATTCTCTACACTGGGTCCGCCAGGCT
CCAGGCAAAGGGCTACAGTGGGTGGCGGTTATCTCATTTGATGGGAATTTTAAACACTTC
GCAGACTCCCTGAGGGGCCGATTCACCATCTCCAGAGACAATTCCAAGAACAGATTCTAT
TTGCAAATGAATGGCCTGAGAGGTGAGGACACGGCTGTATATTACTGTGCGAGAGATGGA
CGTGCTGTTGACGGGTTTAGTGGGATCCTCGACTTCTGGGGCCAGGGAACCCTAGTCAGC
GTCTCCTCAG MAB314 HC variable domain nucleotide sequence (SEQ ID NO: 42)
CAGGTGCAGCTGCAGGAGTCGGGGGGAGGCTTGGTCCAGCCGGGGGGGTCCCTGAAACTC
TCCTGTGCAGTCTCTGGATTCTCCTTCGGTGGCTCTGCAATGCACTGGGTCCGCCAGGCT
TCCGGGAAAGGGCTGGAGTGGATTGGCCATATTAGAAGCGGAGCTAATAATTTCGAGACA
GCATATGCTCCGTCGCTGGATGGCAGGTTCACCATCTCCAGAGACGATTCAAAGAACACG
GCGTATCTGCACATGAACAGCCTGAAAACCGATGACACGGCCATGTATTTCTGCACTACC
GGACTTATAGCGTCAGGTGATGCAAATTTTGACTACTGGGGCCAGGGAACCCAGGTCACC
GTCTCCTCGG MAB316 HC variable domain nucleotide sequence (SEQ ID NO: 43)
CAGGTGCAGCTGGTGCAGTCTGGGGGAGGCGTGGTCCAGCCTGGGAGGTCCCTGACACTC
TCCTGTGCAGCCTCTGGATTCACCTTCAGTGGCTTTTCTCTACACTGGGTCCGCCAGGCT
CCAGGCAAGGGGCTACAGTGGGTGGCGGTTATCTCATTTGATGGGAACCATAAACACTTC
GCAGACTCCCTGAAGGGCCGATTCACCATCTCCAGAGACAATTCCAAGAACACATTGTAT
TTGCAAATTAATGACCTGAGAGGTGAGGACACGGCTGTATATTACTGTGCGAGAGATGGA
CGTGCTGTTGACGGGTTTAGTGGGATTCTCGACTTCTGGGGCCAGGGAACCCTGGTCAGC
GTCTCCTCAG MAB319 HC variable domain nucleotide sequence (SEQ ID NO: 44)
CAGGTGCAGCTGGTGGAGTCTGGGGGAGGCGTGGTCCAGCCTGGGAGGTCCCTGAGACTC
TCCTGTTCAGCCTCAGGATTCACCTTCAGTGACTATAATCTACACTGGGTCCGCCAGGCT
CCAGGCAAGGGGCTGGAGTGGGTGGCAGTCATCTCAATTGATGGAAGCGATAAACACCAC
GCAGACTCCGTGAAGGGCCGATTCACCGTCTCCAGAGACAATTCCAAGAACACAGTGAGT
CTACAAATGGACAGCCTGAGACCTGAAGCACGGCTGTATATTACTGTGCGAGAGATGGC
CGTAGTGTGGGCGGCTACAGTGGGATCCTCGACCCCTGGGGCCAGGGAACCCTGGTCACC
GTCTCCTCAG MAB321 HC variable domain nucleotide sequence (SEQ ID NO: 45)
GAGGTGCAGCTGGTGGAGTCCGGAGCAGAGGTGAAAAAGCCCGGGGAGTCTCTGAAGATC
TCCTGTCAGGGTTCTGGATACAGGTTTACCAATTACTGGATCGCCTGGGTGCGCCAGATG
CCCGGGAAAGGCCTGGAGTGGATGGGGATCATCTATCCTGGTGACTCTGATACCAGATAT
CACCCGTCCTTCCAAGGCCAGGTCACCATCTCATCCGACAAATCCCTCAACACCGCCTAC
CTGCAGTGGAGCAGCCTGAAGCCCTCGGACACCGCCGTGTATTACTGTGCGAGACACCAC
TGCCTTAGTACCAACTGCCAAACCGCAGTGGCTGGATATAATGACTACTGGGGCCAGGGA
AACCCTGGTCGCCGTCTCCTCAG MAB322 HC variable domain nucleotide sequence (SEQ ID NO: 46)
CAGGTGCAGCTGGTGGAGTCCGGGGGAGGCGTGGTCCAGCCTGGGAGGTCCCTGAGACTT
TCCTGTTCAGCCTCTGGATTCACCTTCACCAACTATAACATGCACTGGGTCCGCCAGGCT
CCAGGCAAGGGGCTGGAGTGGGTGGCAGTTACGTCAAAAGATGGAAACGAAAACACTTT
GCAGACTCCGTGAAGGGCCGATTCACCATCTCCAGAGACAATTCCAAGAACACGCTGTAT
CTGGAAATGAACACCCTGACAGCTGAGGACACGGCGATATATTACTGTACGAGAGATGGG
CGAACCGATGGTACTGGGTACTCCGGTATTCTTGATATCTGGGGCCAAGGGACAAAGGTC
ACCGTCTCCTCA MAB323 HC variable domain nucleotide sequence (SEQ ID NO: 47)
CAGGTGCAGCTGGTGCAGTCTGGGGGAGGGGTGGTCCAGCCTGGGAGGTCCCTGAGACTC
TCCTGTGCAGCCTCTGGATTCACCTTCAGTAACTTTGCTATGCACTGGGTCCGCCAGGCT
CCAGGCAAGGGGCTGGAGTGGGTGGCAGTTATATCAAATGCTGGAAGGGAAACACACTAC
GCAGACTCCGTGAAGGGCCGATTCACCGTCTCCAGAGACAATTCCAAGAATATGTTGTCT
CTGCAAATGAACAGCCTGAGAGGTGAGGACACGGCTGTGTATTACTGTGCGAGAGATGGG
CGAACCGATGGTAGTGGCTATTCCGGTGTTCTTGATATCTGGGCCCAAGGGACACTGGTC
ACTGTCTCCTCA MAB338 HC variable domain nucleotide sequence (SEQ ID NO: 48)
CAGGTGCAGCTGGTGGAGTCCGGGGGAGGCGTGGTCCAGCCTGGGAGGTCCCTGAGACT
CTCCTGTTCAGGCTCTGGATTCACCTTCAGTGACTATAATCTACACTGGGTCCGCCAGGCT
CCAGGCAAGGGGCTGGAATGGGTGGCAGTCATTTCAATTGATGGAACTAATAAACACCA
CGCAGACTCCGTGAAGGGCCGATTCACCATCTCCAGAGACAACTCCAAGAATACAGTGA
ATCTGGAAATGAGTCGGCTGAAAGCAGAAGACACGGCTGTATATTACTGTGTGAGAGAT
GGGCGAAGTATTGGCGGCTACAGTGGAATCTTCGACCCCTGGGGCCAGGGAACCCTGGT
CACCGTCTCCTCA
```

SEQUENCE LISTING

MAB343 HC variable domain nucleotide sequence (SEQ ID NO: 49)
CAGGTGCAGCTGCAGGAGTCAGGGGGAGGCGTGGTCCAGCCTGGGAGGTCCCTGAGACTC
TCCTGTGCAGCCTCTGGATTCACCTTCAATACCTACAATATGCACTGGGTCCGCCAGGCT
CCAGGCAAGGGGCTGGAGTGGGTGGCAGTTATATCAAATGATGGAACCTATAAATACTCC
GCTGACTCCGTGAAGGGCCGATTCAGCATCTCCAGAGGCAATTCCAAGAACACGTTGTAT
CTGCAGATGAACAGCCTGAGACCTGACGACACGGCTGTATATTACTGTGCGAGAGATGGG
CGTAGTGTTGGCGGGTTTAGTGGGATCCTCGACCCCTGGGGCCAGGGAACCCTGGCCACC
GTCTCCTCA MAB345 HC variable domain nucleotide sequence (SEQ ID NO: 50)
CAGGTGCAGCTGGTGGAGTCCGGGGGAGGCGTGGTCCAGCCTGGGAGGTCCCTGAGACTC
TCCTGTGCAGCCTCTGGATTCACCTTCAGTGACTACAATATGCACTGGGTCCGCCAGGCT
CCAGGCAAGGGGCTGGAGTGGGTGGCAGTTATTTCAATTGATGGAACGTATAAATACTCC
GCTGACTCCGTGGCGGGCCGATTCAGTCTCTCCAGAGACAATTCCAAGAACACGTTGTAT
TTGCAGATGAATAGTCTGAGACCTGACGACACGGCTATATATTATTGCGCGAGAGATGGG
CGTAGTGTTGGCGGGTTTAGTGGGATCCTCGACCCCTGGGGCCAGGGAACCCTGGTCACC
GTCTCCTCAG Human LC nucleotide sequence of constant kappa region
(SEQ ID NO: 51)
ACTGTGGCTGCACCATCTGTCTTCATCTTCCCGCCATCTGATGAGCAGTTGAAATCTGGA
ACTGCTAGCGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCACAAAGAGC
TTCAACAGGGGAGAGTGTTAG MAB297 and MAB322 LC variable domain nucleotide sequence
(SEQ ID NO: 52)
GAAATTGTAATGACGCAGTCTCCAGCCACCCTGTCTTTGTCTCCAGGGGAAAGAGCCACC
CTCTCCTGCAGGGCCAGTCAGAGTGTTGGCGGCTACTTAGCCTGGTACCAACAGAAACCT
GACCAGGCTCCCAGGCTCCTCATCTATGATGTTTCCAATAGGGCCGCTGGCATCCCAGCC
AGGTTCAGTGGCAGTGGGTCTGGGACAGACTTCACTCTCACCATCAGCAGCCTGGAGCCT
GAAGATTTTGCAGTTTATTACTGTCAGCAGCGGAACACCTGGCCTCCGCTCACTTTCGGC
GGAGGGACCAAGGTGGAGATCAAACGA MAB309 LC variable domain nucleotide sequence (SEQ ID NO: 53)
GAAATTGTGTTGACGCAGTCTCCAGCCACCCTGTCTTTGTCTCCAGGGGATAGAGCCACC
CTCTCCTGCAGGGCCAGTCAGAGTGTTGGCAGGTACTTAGCCTGGTACCAACAAAAACCT
GGCCAGGCTCCCAGGCTCCTCATCTATGATGCTTCCGACAGGGCCACTGGCATCTCAGCC
AGGTTCAGTGGCAGTGGGTCTGGGACAGATTTCACTCTCACCATCAGCAGCCTGGAGCCT
GAAGATTTTGCAGTCTATTACTGTCAGCAGCGGAGCAGCTGGCCGCCGCTCACTTTCGGC
GGAGGGACCAAGGTGGAGATCAAACGA MAB310 LC variable domain nucleotide sequence (SEQ ID NO: 54)
GAAATTGTGTTGACTCAGTCTCCAGCCACCCTGTCTTTGTCTCCAGGGGATAGAGCCACC
CTCTCCTGCAGGGCCAGTCAGACTGTTGGCAGGTACTTAGCCTGGTACCAACAGAAACCT
GGCCAGGCTCCCAGGCTCCTCATCTATGATGCTTCCGACAGGGCCACTGGCATCTCAGCC
AGGTTCAGTGGCAGTGGGTCTGGGACAGATTTCACTCTCACCATCAGCAGCCTAGAGCCT
GAAGATTTTGCAGTCTATTACTGTCAGCAGCGGAGCAACTGGCCTCCGCTCACTTTCGGC
GGAGGGACCAAGGTGGAGATCAAACGA MAB313 LC variable domain nucleotide sequence (SEQ ID NO: 55)
GAAATTGTGATGACTCAGTCTCCAGCCACCCTGTCTTTGTCTCCAGGGGAAAGAGCCACC
CTCTCCTGCAGGGCCAGTCAGAGTGTTGGCAGATACTTAACTTGGTTCCAGCAGAAACCT
GGCCAGGCTCCCAGGCTCCTCATCTATGATGCTTCCGAGAGGGCCACTGGCATCCCAGCC
AGGTTCAGTGGCAGTGGGTCTGGGACAGACTTCACTCTCACCATCAGCAGCCTAGAGCCT
GAAGATTTTGCAGTTTATTACTGTCAACAGCGTGCTAACTGGCCTCCGCTCACTTTCGGC
GGAGGGACCAAGGTGGAGATCAAACGA MAB314 LC variable domain nucleotide sequence (SEQ ID NO: 56)
GAAATTGTGATGACCCAGTCTCCAGGCACCCTGTCCTTGTTTCCAGGGGAAAGAGCCACC
CTCTCCTGCAGGGCCAGTCAGACTGTTAGGAACGGCTACTTAGCCTGGTACCAGCAGAAA
CCTGGCCAGGCTCCCAGGCTCCTCATCTATGGTGCTTCCATCAGGGCCACTGGCATCCCA
GACAGGTTCAGTGGCAGTGGGTCTGAGACAGACTTCACCCTCAGCATCACCAGAGTGGAG
CCTGAAGATTTTGCAGTTTATTACTGTCAACAGTATGGAAGGTTATCGTCCACTTTTGGC
CAGGGGACCAAGCTGGACCTCAAACGA MAB316 LC variable domain nucleotide sequence (SEQ ID NO: 57)
GAAATTGTGATGACCCAGTCTCCAGCCACCCTGTCTTTGTCTCCAGGGGAAAGAGCCACC
CTCTCCTGCAGGGCCAGTCAGAGTGTTGGCAGATACTTAACTTGGTTCCAGCAGAAACCT
GGCCAGGCTCCCAGGCTCCTCATCTATGATGCTTCCGAGAGGGCCACTGGCGTCCCAGCC
AGGTTCAGTGGCAGTGGGTCTGGGACAGACTTCACTCTCACCATCAGCAGCCTAGAGCCT
GAAGATTTTGCAGTTTATTACTGTCAACAGCGTAGTAACTGGCCTCCGCTCACTTTCGGC
GGAGGGACCAAGGTGGAGATCAAAC

SEQUENCE LISTING

MAB318 LC variable domain nucleotide sequence (SEQ ID NO: 58)
GAAGTTGTGCTGACGCAGTCTCCAGCCACCCTGTCTTTGTCTCCAGGGGATAGAGCCACC
CTCTCCTGCAGGGCCAGTCAGACTGTTGGCAGGTACTTAGCCTGGTACCAACAAAAACCT
GGCCAGGCTCCCAGGCTCCTCATCTATGATGCTTCCGACAGGGCCACTGGCATCTCAGCC
AGGTTCAGTGGCAGTGGGTCTGGGACAGATTTCACTCTCACCATCGGCAGCCTGGAGCCT
GAAGATTTTGCAGTCTATTACTGTCAGCAGCGGAGCAGCTGGCCGCCGCTCACTTTCGGC
GGAGGGACCAAGGTGGAGATCAAAC MAB319 LC variable domain nucleotide sequence (SEQ ID NO: 59)
GAAATTGTGTTGACGCAGTCTCCAGCCACCCTGTCTTTGTCTCCAGGGGAAAGGGCCACC
CTCTCCTGCAGGGCCAGTCAGAGTGTTGGCAGCTACTTAGCCTGGTATCAACAGAAACCT
GGCCAGGCTCCCAGGCTCCTCATCTATGATGCATCCGAGAGGGCCACTGGCATCCCAGCC
AGGTTCAGTGGCAGTGGGTCTGGGACAGACTTCACTCTCACCATCAGCAGCCTAGAGCCT
GAAGATGTTGCAGTTTATTACTGTCAGCAGCGTAACAACTGGCCTCCGCTCACCTTCGGC
GGAGGGACCAAGGTGGAGATCAAAC MAB321 LC variable domain nucleotide sequence (SEQ ID NO: 60)
GAAATTGTGATGACCCAGTCTCCAGACTCCCTTGCTGTGTCTCTGGGCGAGAGGGCCACC
ATCAACTGCAAGTCCAGTCAGAGTATTTTATTCAGCTCCAAGAATCAGAACCACTTAGCT
TGGTACCAGCAGAAACCAGGACAGCCTCCTAAGCTGCTGATTTACTGGGCATCTACCCGG
GAATCCGGGGTCCCCGACCGATTCAGTGGCAGCGGGTCTGGGACAGATTTCACTCTCACC
ATCAGCAGCCTCCAGGCTGAAGATGTGGCAGTTTATTACTGTCAGCAATATTATAATATT
CCTCACACTTTCGGCGGAGGGACCAAGGTGGAGATCAAA MAB323 LC variable domain nucleotide sequence (SEQ ID NO: 61)
GAAATTGTGTTGACTCAGTCTCCAGCCACCTTGTCTTTGTCTCCAGGGGAAAGAGCCACC
CTCTCCTGCCGGGCCAGTCAGAGTGTTAACCGCTACTTAGCCTGGTTCCAACACAGACCT
GGCCAGCCTCCCAGGCTCCTCATCTATGATGCGTCCAAGAGGGCCACTGGCATCCCAGCC
AGGTTCAGTGGCAGTGGGTCTGGGACAGACTTCACTCTCACCATCAGCAGCCTAGAGCCT
GAAGATTTTGCAGTTTATTACTGTCAGCAGCGTAGCAACTGGCCGCTCACTTTCGGCGGA
GGGACCAAGGTGGAGATCAAG MAB338 LC variable domain nucleotide sequence (SEQ ID NO: 62)
GAAATTGTGTTGACCCAGTCTCCAGCCACCCTGTCTTTGTCTCCAGGGGAAAGAGCCACC
CTCTCCTGCAGGGCCAGTCAGAGTGTTGACAGGTACTTAGCCTGGTACCAACAGAAACCT
GGCCAGGCTCCCAGACTCCTCATCTATGATGCATCCCAGAGGGCCACTGGCATCCCAGCC
AGGTTCAGTGGCAGTGGGTCCGGGACAGACTTCACTCTCGCCATCAGCAGCCTGGAGCCT
GAAGATGTTGCAGTTTATTACTGTCAGCAGCGTAGTAACTGGCCTCCGCTCACCTTCGGC
GGAGGGACCAAAATAGAGATCAAA MAB343 LC variable domain nucleotide sequence (SEQ ID NO: 63)
GAAATCGTGATGACCCAGTCTCCAGCCACCCTGTCTTTGTCTCCAGGGGATAGAGCCACC
CTCTCCTGCAGGGCCAGTCAGAGTGTTGGCAGCTACTTAGCCTGGTACCAACAGAAACCT
GGCCAGGCTCCCAGGCTCCTCATCTATGATGCTTCCGACAGGGCCACTGGCATCCCAGCC
AGGTTCAGTGGCAGTGGGTCTGGGACAGATTTCACTCTCACCATCAGCAGCCTAGAGCCT
GAAGATTTTGCAGTTTATTACTGTCAGCAGCGTAGCAACTGGCCTCCGCTCACTTTCGGC
GGAGGGACCAAGGTGGAGATCAAAC MAB345 LC variable domain nucleotide sequence (SEQ ID NO: 64)
GAAATTGTGATGACCCAGTCTCCAGCCACCCTGTCTTTGTCTCCAGGGGATAGAGCCACC
CTCTCCTGCAGGGCCAGTCAGAGTGTTGGCAGCTACTTAGCCTGGTACCAACAGAAACCT
GGCCAGGCTCCCAGGCTCCTCATGTATGATTCTTCCGTCAGGGCCACTGGCATCCCAGCC
AGGTTCAGTGGCAGCGGGTCTGGGACAGATTTCACTCTCACCATCAGCAGCCTAGAGCCT
GAAGATTTTGCAGTTTATTACTGTCAGCAGCGTAACAACTGGCCTCCGCTCACTTTCGGC
GGAGGGACCAAGGTGGAGATCAAA Human LC nucleotide sequence of constant kappa region
(SEQ ID NO: 65)
ACTGTGGCTGCACCATCTGTCTTCATCTTCCCGCCATCTGATGAGCAGTTGAAATCTGGA
ACTGCTAGCGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCACAAAGAGC
TTCAACAGGGGAGAGTGTTAG Human LC nucleotide sequence of constant lambda region
(SEQ ID NO: 66)
GGTCAGCCCAAGGCTGCCCCCTCTGTCACTCTGTTCCCGCCCTCTAGCGAGGAGCTTCAA
GCCAACAAGGCCACACTGGTGTGTCTCATAAGTGACTTCTACCCGGGAGCCGTGACAGTG
GCCTGGAAGGCAGATAGCAGCCCCGTCAAGGCGGGAGTGGAGACCACCACACCCTCCAAA
CAAAGCAACAACAAGTACGCGGCCAGCAGCTATCTGAGCCTGACGCCTGAGCAGTGGAAG
TCCCACAGAAGCTACAGCTGCCAGGTCACGCATGAAGGGAGCACCGTGGAGAAGACAGTG
GTCCCTGCAGAATGCTCT

The invention claimed is:

1. Recombinant host cells comprising an expression system or expression systems for a monoclonal antibody (mAb) that is specifically immunoreactive with cytomegalovirus glycoprotein B (CMV gB) protein or an antigen binding fragment thereof wherein:
 (a) the heavy chain comprises the CDR1, CDR2 and CDR3 regions of the variable region of MAB4A2 (SEQ ID NO:2); or
 (b) comprises the CDR1, CDR2 and CDR3 regions of the heavy chain variable region of MAB19B10 (SEQ ID NO:6); or
 (c) comprises the CDR1, CDR2 and CDR3 regions of the heavy chain variable region of MAB313 (SEQ ID NO:13); or
 (d) comprises the CDR1, CDR2 and CDR3 regions of the heavy chain variable region of MAB338 (SEQ ID NO:20); or
 (e) comprises the CDR1, CDR2 and CDR3 regions of the heavy chain variable region of MAB345 (SEQ ID NO:22).

2. The cells of claim 1 wherein the mAb is in the form of a complete antibody.

3. The cells of claim 1 wherein the mAb is a bi-specific antibody.

4. The cells of claim 1 wherein the light chain of said mAb
 in (a) comprises the CDR1, CDR2 and CDR3 regions of light chain variable region of MAB4A2 (SEQ ID NO:4); and
 in (b) comprises the CDR1, CDR2 and CDR3 regions of light chain variable region of MAB19B10 (SEQ ID NO:8); and
 in (c) comprises the CDR1, CDR2 and CDR3 regions of light chain variable region of MAB313 (SEQ ID NO:27); and
 in (d) comprises the CDR1, CDR2 and CDR3 regions of light chain variable region of MAB338 (SEQ ID NO:34); and
 in (e) comprises the CDR1, CDR2 and CDR3 regions of light chain variable region of MAB345 (SEQ ID NO:36).

5. The cells of claim 1 wherein in said mAb or fragment,
 (a) the heavy chain variable region comprises that of MAB4A2 (SEQ ID NO:2); or
 (b) the heavy chain variable region comprises that of MAB19B10 (SEQ ID NO:6); or
 (c) the heavy chain variable region comprises that of MAB313 (SEQ ID NO:13); or
 (d) the heavy chain variable region comprises that of MAB338 (SEQ ID NO:20); or
 (e) the heavy chain variable region comprises that of MAB345 (SEQ ID NO:22).

6. The cells of claim 5 wherein in said mAb or fragment,
 in (a) the light chain variable region comprises that of MAB4A2 (SEQ ID NO:4); and
 in (b) the light chain variable region comprises that of MAB19B10 (SEQ ID NO:8); and
 in (c) the light chain variable region comprises that of MAB313 (SEQ ID NO:27); and
 in (d) the light chain variable region comprises that of MAB338 (SEQ ID NO:34); and
 in (e) the light chain variable region comprises that of MAB345 (SEQ ID NO:36).

7. The cells of claim 1 wherein said monoclonal antibody is MAB345 (ATCC deposit number PTA-121705) or an antigen binding fragment thereof.

8. Monoclonal antibodies including antigen-binding fragments thereof produced by the cells of claim 1.

9. A pharmaceutical composition that comprises a therapeutically effective amount of the monoclonal antibody or fragment of claim 8, along with a pharmaceutically acceptable excipient.

10. A pharmaceutical composition that comprises a therapeutically effective amount of the monoclonal antibody or fragment produced by the cells of claim 1, along with a pharmaceutically acceptable excipient.

11. The pharmaceutical composition of claim 9 that further contains an additional pharmaceutical agent, along with a pharmaceutically acceptable excipient.

12. The pharmaceutical composition of claim 10 that further contains an additional pharmaceutical agent, along with a pharmaceutically acceptable excipient.

13. Monoclonal antibodies including antigen-binding fragments thereof produced by the cells of claim 7.

14. A pharmaceutical composition that comprises a therapeutically effective amount of the monoclonal antibody or fragment of claim 13, along with a pharmaceutically acceptable excipient.

15. A pharmaceutical composition that comprises a therapeutically effective amount of the monoclonal antibody or fragment produced by the cells of claim 7, along with a pharmaceutically acceptable excipient.

16. The pharmaceutical composition of claim 14 that further contains an additional pharmaceutical agent, along with a pharmaceutically acceptable excipient.

17. The pharmaceutical composition of claim 15 that further contains an additional pharmaceutical agent, along with a pharmaceutically acceptable excipient.

* * * * *